(12) United States Patent
Chen et al.

(10) Patent No.: US 9,545,203 B2
(45) Date of Patent: Jan. 17, 2017

(54) SYSTEMS AND METHODS FOR CARDIOMYOCYTE CONDUCTION SPEED MAPPING

(71) Applicant: Guangren Chen, Porter Ranch, CA (US)

(72) Inventors: Guangren Chen, Porter Ranch, CA (US); Lingling Yao, Shanghai (CN)

(73) Assignee: Guangren Chen, Porter Ranch, CA (US)

(*) Notice: Subject to any disclaimer, the term of this patent is extended or adjusted under 35 U.S.C. 154(b) by 0 days.

(21) Appl. No.: 14/749,696

(22) Filed: Jun. 25, 2015

(65) Prior Publication Data

US 2015/0351650 A1 Dec. 10, 2015

Related U.S. Application Data

(63) Continuation-in-part of application No. 14/662,996, filed on Mar. 19, 2015, now Pat. No. 9,339,204, which (Continued)

(51) Int. Cl.
| | |
|---|---|
| *A61B 5/02* | (2006.01) |
| *A61B 5/0456* | (2006.01) |
| *A61B 5/044* | (2006.01) |
| *A61B 5/042* | (2006.01) |
| *A61B 5/00* | (2006.01) |
| *A61B 5/04* | (2006.01) |
| *A61B 5/0452* | (2006.01) |

(52) U.S. Cl.
CPC .......... *A61B 5/02028* (2013.01); *A61B 5/044* (2013.01); *A61B 5/04017* (2013.01); *A61B 5/0422* (2013.01); *A61B 5/0452* (2013.01); *A61B 5/0456* (2013.01); *A61B 5/743* (2013.01)

(58) Field of Classification Search
CPC .............. A61B 5/0006; A61B 5/04012; A61B 5/04014; A61B 5/0402; A61B 5/0452; A61B 5/0464; A61B 5/0468
USPC ........................................ 600/516, 517, 523
See application file for complete search history.

(56) References Cited

U.S. PATENT DOCUMENTS 4,157,711 A * 6/1979 Yotam ................ A61B 5/04012
600/521
4,751,931 A * 6/1988 Briller .................. A61B 5/0428
600/509

(Continued)

*Primary Examiner* — Christopher A Flory
(74) *Attorney, Agent, or Firm* — John R. Kasha; Kelly L. Kasha; Kasha Law LLC

(57) ABSTRACT

Systems and methods are provided to display discrete conduction timing values of layers of the ventricles. Electrical impulses are detected using two or more electrodes placed proximate to a beating heart and are converted to an ECG waveform for each heartbeat of the beating heart. One or more subwaveforms within Q, R, S, and T waveforms of the ECG waveform for each heartbeat or in an interval between the Q, R, S, and T waveforms are detected that represent the depolarization or repolarization of anatomically distinct layers of the ventricles of the beating heart. A conduction timing value is calculated for each of the one or more subwaveforms for each electrode of the two or more electrodes for each heartbeat of the beating heart. At least one conduction timing value is displayed for at least one subwaveform for each electrode for at least one heartbeat of the beating heart.

20 Claims, 26 Drawing Sheets

Related U.S. Application Data is a continuation of application No. PCT/US2015/020828, filed on Mar. 16, 2015.

(60) Provisional application No. 62/008,435, filed on Jun. 5, 2014, provisional application No. 62/017,188, filed on Jun. 25, 2014.

(56) References Cited

U.S. PATENT DOCUMENTS

| | | | | |
|---|---|---|---|---|
| 6,397,100 B2* | 5/2002 | Stadler | ............... | A61B 5/04011 128/901 |
| 6,931,273 B2* | 8/2005 | Groenewegen | .... | A61B 5/04023 600/509 |
| 7,787,951 B1* | 8/2010 | Min | .................. | A61B 5/04012 607/17 |
| RE43,569 E * | 8/2012 | Olson | ................ | A61B 5/04011 600/450 |
| 8,306,265 B2* | 11/2012 | Fry | ....................... | A61B 5/0452 348/143 |
| 2002/0138014 A1* | 9/2002 | Baura | .................... | A61B 5/029 600/526 |
| 2003/0120165 A1* | 6/2003 | Bjorling | ................. | A61N 1/056 600/515 |
| 2004/0260169 A1* | 12/2004 | Sternnickel | ........ | A61B 5/04007 600/409 |
| 2005/0105717 A1* | 5/2005 | Lawrie | .................. | H03G 7/007 379/388.01 |
| 2006/0247698 A1* | 11/2006 | Burnes | ................. | A61N 1/3627 607/9 |
| 2006/0264768 A1* | 11/2006 | Satin | .................. | A61B 5/04525 600/509 |
| 2007/0273504 A1* | 11/2007 | Tran | .................... | A61B 5/0022 340/539.12 |
| 2007/0276270 A1* | 11/2007 | Tran | .................... | A61B 5/0022 600/508 |
| 2008/0001735 A1* | 1/2008 | Tran | .................... | G06F 19/3418 340/539.22 |
| 2008/0004904 A1* | 1/2008 | Tran | .................... | A61B 5/0006 705/2 |
| 2008/0109041 A1* | 5/2008 | de Voir | .............. | A61B 5/04017 607/7 |
| 2009/0227876 A1* | 9/2009 | Tran | .................... | A61B 5/0022 600/483 |
| 2009/0318779 A1* | 12/2009 | Tran | .................... | A61B 5/0022 600/301 |
| 2011/0115624 A1* | 5/2011 | Tran | .................... | G06F 19/3418 340/540 |
| 2011/0181422 A1* | 7/2011 | Tran | .................... | G06F 19/3418 340/573.1 |
| 2011/0201951 A1* | 8/2011 | Zhang | .................. | A61B 5/0456 600/509 |
| 2011/0245702 A1* | 10/2011 | Clark | ................. | A61B 5/04284 600/523 |
| 2012/0004564 A1* | 1/2012 | Dobak, III | ............. | A61B 5/021 600/510 |
| 2012/0092157 A1* | 4/2012 | Tran | .................... | G06F 19/3418 340/539.12 |
| 2012/0095352 A1* | 4/2012 | Tran | .................... | A61B 5/0022 600/490 |
| 2012/0157822 A1* | 6/2012 | van Dam | ............. | A61B 5/0402 600/411 |
| 2012/0283587 A1* | 11/2012 | Gosh | .................... | A61B 5/0402 600/510 |
| 2012/0284003 A1* | 11/2012 | Gosh | .................... | A61B 5/0402 703/2 |
| 2012/0330109 A1* | 12/2012 | Tran | .................... | A61B 5/0022 600/301 |
| 2013/0009783 A1* | 1/2013 | Tran | .................... | G06F 19/3418 340/669 |
| 2013/0172691 A1* | 7/2013 | Tran | ....................... | A61B 8/488 600/301 |
| 2013/0231574 A1* | 9/2013 | Tran | .................... | A61B 5/0022 600/479 |
| 2014/0357995 A1* | 12/2014 | Brumfield | ............ | A61B 5/7282 600/438 |
| 2015/0351653 A1* | 12/2015 | Chen | .................... | A61B 5/0452 600/516 |

* cited by examiner

| DATE | LEAD | | | | | | | | | | /s |
|---|---|---|---|---|---|---|---|---|---|---|---|
| 2014-03 | I | 0.02 | 0.01 | 0.01 | 0.01 | 0.01 | 0.02 | 0.02 | 0.02 | 0.02 | 0.01 |
| 2014-03 | II | 0.02 | 0.01 | 0.01 | 0.03 | 0.05 | 0.06 | 0.08 | 0.08 | 0.08 | 0.06 |
| 2014-03 | III | 0.02 | 0.01 | 0.01 | 0.02 | 0.03 | 0.04 | 0.05 | 0.05 | 0.04 | 0.03 |
| 2014-03 | aVR | 0.03 | 0.03 | 0.03 | 0.01 | 0.01 | 0.03 | 0.03 | 0.03 | 0.03 | 0.03 |
| 2014-03 | aVL | 0.01 | 0.01 | 0.01 | 0.01 | 0.01 | 0.01 | 0.01 | 0.01 | 0.01 | 0.01 |
| 2014-03 | aVF | 0.03 | 0.02 | 0.01 | 0.02 | 0.03 | 0.05 | 0.06 | 0.06 | 0.06 | 0.04 |
| 2014-03 | V1 | 0.02 | 0.02 | 0.02 | 0.01 | 0.02 | 0.03 | 0.04 | 0.05 | 0.05 | 0.03 |
| 2014-03 | V2 | 0.02 | 0.02 | 0.01 | 0.02 | 0.03 | 0.04 | 0.04 | 0.05 | 0.05 | 0.03 |
| 2014-03 | V3 | 0.02 | 0.02 | 0.01 | 0.01 | 0.02 | 0.04 | 0.05 | 0.05 | 0.05 | 0.03 |
| 2014-03 | V4 | 0.02 | 0.02 | 0.03 | 0.03 | 0.03 | 0.05 | 0.05 | 0.05 | 0.05 | 0.03 |
| 2014-03 | V5 | 0.02 | 0.01 | 0.02 | 0.02 | 0.03 | 0.05 | 0.06 | 0.05 | 0.05 | 0.03 |
| 2014-03 | V6 | 0.02 | 0.01 | 0.02 | 0.02 | 0.03 | 0.04 | 0.06 | 0.05 | 0.05 | 0.03 |

MALE, 35 YRS OLD, NORMAL

EACH LEAD NORMAL PHYSIOLOGICAL CONDUCTION RAGE: 0.01 - 0.06 ± 0.03 /s
<MALE: 0.06 ± 0.05 /s

| LEAD | | | | | | | | | | /s |
|---|---|---|---|---|---|---|---|---|---|---|
| I | 0.05 | 0.03 | 0.03 | 0.02 | 0.04 | 0.03 | 0.06 | 0.05 | 0.02 | 0.04 |
| II | 0.04 | 0.04 | 0.02 | 0.01 | 0.09 | 0.02 | 0.05 | 0.04 | 0.04 | 0.03 |
| III | 0.01 | 0.03 | 0.04 | 0.06 | 0.02 | 0.08 | 0.04 | 0.04 | 0.09 | 0.04 |
| aVR | 0.05 | 0.03 | 0.02 | 0.01 | 0.03 | 0.03 | 0.06 | 0.05 | 0.03 | 0.03 |
| aVL | 0.03 | 0.03 | 0.03 | 0.01 | 0.02 | 0.01 | 0.04 | 0.03 | 0.04 | 0.03 |
| aVF | 0.02 | 0.02 | 0.02 | 0.01 | 0.02 | 0.05 | 0.02 | 0.02 | 0.02 | 0.02 |
| V1 | 0.02 | 0.09 | 0.04 | 0.04 | 0.04 | 0.05 | 0.06 | 0.06 | 0.04 | 0.04 |
| V2 | 0.08 | 0.08 | 0.07 | 0.07 | 0.07 | 0.07 | 0.05 | 0.05 | 0.07 | 0.07 |
| V3 | 0.03 | 0.03 | 0.02 | 0.00 | 0.02 | 0.01 | 0.01 | 0.01 | 0.03 | 0.02 |
| V4 | 0.04 | 0.05 | 0.04 | 0.02 | 0.03 | 0.02 | 0.00 | 0.02 | 0.03 | 0.03 |
| V5 | 0.05 | 0.06 | 0.07 | 0.08 | 0.09 | 0.09 | 0.11 | 0.10 | 0.08 | 0.08 |
| V6 | 0.04 | 0.04 | 0.06 | 0.08 | 0.06 | 0.08 | 0.09 | 0.08 | 0.06 | 0.06 |

2500

| ID |
|---|
| 0000031 |
| 0000032 |
| 0000033 |
| 0000034 |
| 0000035 |
| 0000037 |

| DATE | T |
|---|---|
| 2014-03-02 | 0 |
| 2014-03-02 | 0 |
| 2014-03-02 | 0 |
| 2014-03-02 | 0 |
| 2014-03-02 | 0 |
| 2014-03-01 | 1 |
| 2014-03-01 | 1 |
| 2014-03-01 | 1 |

FIG. 25

SYSTEMS AND METHODS FOR CARDIOMYOCYTE CONDUCTION SPEED MAPPING

CROSS REFERENCE TO RELATED APPLICATION

This application is a continuation in part of U.S. patent application Ser. No. 14/662,996, filed Mar. 19, 2015, which is a continuation of PCT Application No. PCT/US15/20828, filed Mar. 16, 2015, which claims the benefit of U.S. Provisional Patent Application Ser. No. 62/008,435, filed Jun. 5, 2014, and this application claims the benefit of U.S. Provisional Patent Application Ser. No. 62/017,188, filed Jun. 25, 2014, the content of all of which is incorporated by reference herein in their entireties.

INTRODUCTION

Electrical signals produced by a human heart were observed through electrodes attached to a patient's skin as early as 1879. Between 1897 and 1911 various methods were used to detect these electrical signals and record a heartbeat in real-time. In 1924, Willem Einthoven was awarded the Nobel Prize in medicine for identifying the various waveforms of a heartbeat and assigning the letters P, Q, R, S, T, U, and J to these waveforms. Since the early 1900s the equipment used for electrocardiography (ECG or EKG) has changed. However, the basic waveforms detected and analyzed have not changed.

An ECG device detects electrical impulses or changes in the electrical potential between two electrodes attached to the skin of a patient as the heart muscle contracts or beats. Electrically, the contraction of the heart is caused by depolarization and repolarization of various parts of the heart muscle. Initially, or at rest, the muscle cells of the heart have a negative charge. In order to cause them to contract, they receive an influx of positive ions $Na^+$ and $Ca^{++}$. This influx of positive ions is called depolarization. The return of negative ions to bring the heart back to a resting state is called repolarization. Depolarization and repolarization of the heart affects different parts of the heart over time giving rise to the P, Q, R, S, T, U, and J waveforms.

FIG. 2 is an exemplary plot 200 of the P, Q, R, S, and T waveforms of a conventional ECG waveform of a heartbeat from a conventional ECG device. The P, Q, R, S, and T waveforms represent electrical conduction through a heart muscle. P waveform 210 represents the propagation of depolarization from the sinoatrial node, to the right and left atriums, and to the atrioventricular node. The sinoatrial node is also referred to as the sinus node, SA node, or SAN. The atrioventricular node is also referred to as the AV node or AVN. The right atrium is also referred to as the RA, and the left atrium is also referred to as the LA.

FIG. 3 is an exemplary diagram 300 of the depolarization of the muscle tissue of a heart that produces P waveform 210 of FIG. 2 as detected by a conventional ECG device. P waveform 210 of FIG. 2 is produced as depolarization propagates from SAN 310 to AVN 340 in FIG. 3. As depolarization propagates from SAN 310 to AVN 340, it also spreads from RA 320 to LA 340. P waveform 210 of FIG. 2 typically has a duration of 80 ms, for example.

PR segment 220 of FIG. 2 represents the propagation of depolarization from the AVN to the Bundle of His, and then to the Bundle Branches. PR segment 230 may also include depolarization to the Purkinje fibers of the inner ventricular walls. The Bundle of His is also referred to as the His Bundle or His. The Bundle Branches include the right bundle branches (RBB) and the left bundle branches (LBB). As shown in FIG. 2, in a conventional ECG, PR segment 220 shows up as a flat line or waveform with no amplitude.

FIG. 4 is an exemplary diagram 400 of the depolarization of the muscle tissue of a heart that produces PR segment 220 of FIG. 2 as detected by a conventional ECG device. PR segment 220 of FIG. 2 is produced as depolarization propagates from AVN 340 to His 450 and then to Bundle Branches 460 that include RBB 461 and LBB 462. PR segment 220 of FIG. 2 typically has a duration of between 50 and 120 ms, for example.

Waveforms Q 230, R 240, and S 250 of FIG. 2 form the QRS complex. The QRS complex represents the propagation of depolarization through the right and left ventricles. The right ventricle is also referred to as RV, and the left ventricle is referred to as LV.

FIG. 5 is an exemplary diagram 500 of the depolarization of the muscle tissue of a heart that produces Q waveform 230, R waveform 240, and S waveform 250 of FIG. 2 as detected by a conventional ECG device. Waveforms Q 230, R 240, and S 250 of FIG. 2 produced as depolarization propagates from Bundle Branches 460 through RV 571 and LV 572. RV 571 and LV 572 have the largest muscle mass in the heart. The QRS complex formed by waveforms Q 230, R 240, and S 250 of FIG. 2 typically has a duration of between 80 and 100 ms, for example.

ST segment 260 of FIG. 2 represents the period during which the ventricles remain depolarized and contracted. As shown in FIG. 2, in a conventional ECG, ST segment 260 shows up as a flat line or waveform with no amplitude. ST segment 260 typically has a duration of between 80 and 120 ms, for example.

The point in FIG. 2 at which the QRS complex ends and ST segment 260 begins is called J point 255. A J waveform (not shown) can sometimes appear as an elevated J point at J point 255 or as a secondary R waveform. A J waveform is usually characteristic of a specific disease. The J waveform is also referred to as the Osborn wave, camel-hump sign, late delta wave, hathook junction, hypothermic wave, prominent J wave, K wave, H wave or current of injury.

T waveform 270 of FIG. 2 represents the repolarization or recovery of the ventricles. T waveform 270 typically has a duration of 160 ms, for example. The interval between the Q and T waveforms is referred to as the QT interval.

FIG. 6 is an exemplary diagram 600 of the repolarization of the muscle tissue of a heart that produces T waveform 270 of FIG. 2 as detected by a conventional ECG device. As shown in FIG. 6, RV 571 and LV 572 are repolarized.

Not shown in FIG. 2 is the U waveform. The U waveform sometimes appears after the T waveform. The U waveform is thought to represent repolarization of the interventricular septum, the papillary muscles, or the Purkinje fibers.

As shown in FIGS. 3 through 6, as a heart beats, electrical signals flow through all the different muscle tissues of the heart. As shown in FIG. 2, for the last 100 years conventional ECG devices have been able to detect some of these signals in the form of the P, Q, R, S, T, U, and J waveforms. These waveforms have aided in the diagnosis and treatment of many heart problems. Unfortunately, however, the P, Q, R, S, T, U, and J waveforms do not provide a complete picture of the operation of all the different muscle tissues of the heart. As a result, improved systems and methods are needed to detect and analyze more information from the electrical signals that flow through all the different muscle tissues of the heart as it is beating. This additional information can be used to diagnose and treat many more heart problems.

BRIEF DESCRIPTION OF THE DRAWINGS

FIG. 23 is an exemplary table showing the timing values for 10 layers of the ventricle recorded at 12 different leads of an ECG for a 35 year-old normal male, in accordance with various embodiments.

FIG. 25 is an exemplary table showing the timing values for 10 layers of the ventricle recorded at 12 different leads of an ECG for a 51 year-old male after percutaneous coronary intervention (PCI, formerly known as angioplasty with stent) who had a left anterior descending artery with 80% proximal, 90% middle, and 70% distal blockage, in accordance with various embodiments.

Before one or more embodiments of the invention are described in detail, one skilled in the art will appreciate that the invention is not limited in its application to the details of construction, the arrangements of components, and the arrangement of steps set forth in the following detailed description. The invention is capable of other embodiments and of being practiced or being carried out in various ways. Also, it is to be understood that the phraseology and terminology used herein is for the purpose of description and should not be regarded as limiting.

DETAILED DESCRIPTION

Computer-Implemented System

Figure 1:
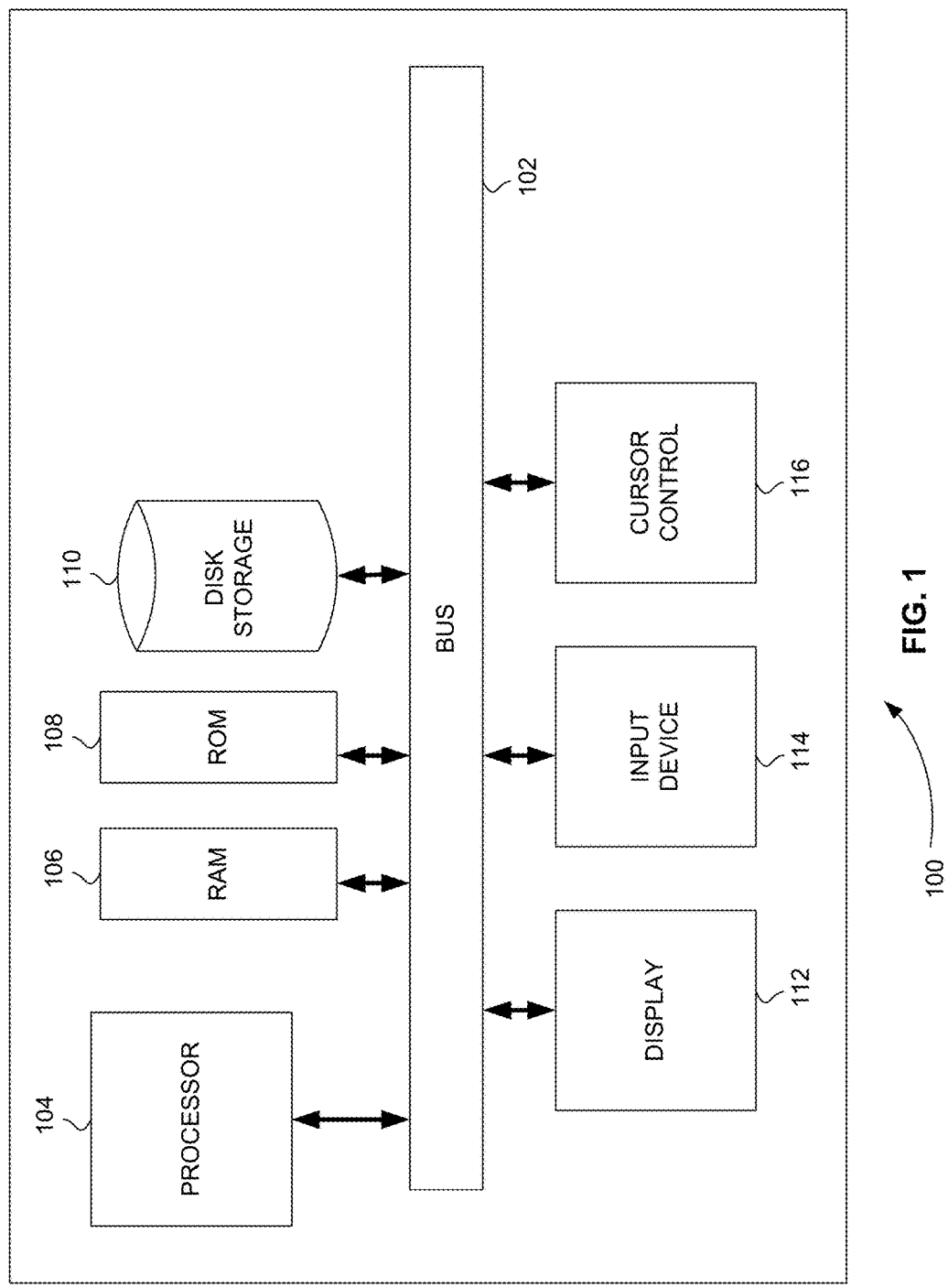
FIG. 1 is a block diagram that illustrates a computer system, in accordance with various embodiments.

FIG. 1 is a block diagram that illustrates a computer system 100, upon which embodiments of the present teachings may be implemented. Computer system 100 includes a bus 102 or other communication mechanism for communicating information, and a processor 104 coupled with bus 102 for processing information. Computer system 100 also includes a memory 106, which can be a random access memory (RAM) or other dynamic storage device, coupled to bus 102 for storing instructions to be executed by processor 104. Memory 106 also may be used for storing temporary variables or other intermediate information during execution of instructions to be executed by processor 104. Computer system 100 further includes a read only memory (ROM) 108 or other static storage device coupled to bus 102 for storing static information and instructions for processor 104. A storage device 110, such as a magnetic disk or optical disk, is provided and coupled to bus 102 for storing information and instructions.

Computer system 100 may be coupled via bus 102 to a display 112, such as a cathode ray tube (CRT) or liquid crystal display (LCD), for displaying information to a computer user. An input device 114, including alphanumeric and other keys, is coupled to bus 102 for communicating information and command selections to processor 104. Another type of user input device is cursor control 116, such as a mouse, a trackball or cursor direction keys for communicating direction information and command selections to processor 104 and for controlling cursor movement on display 112. This input device typically has two degrees of freedom in two axes, a first axis (i.e., x) and a second axis (i.e., y), that allows the device to specify positions in a plane.

A computer system 100 can perform the present teachings. Consistent with certain implementations of the present teachings, results are provided by computer system 100 in response to processor 104 executing one or more sequences of one or more instructions contained in memory 106. Such instructions may be read into memory 106 from another computer-readable medium, such as storage device 110. Execution of the sequences of instructions contained in memory 106 causes processor 104 to perform the process described herein. Alternatively hard-wired circuitry may be used in place of or in combination with software instructions to implement the present teachings. Thus implementations of the present teachings are not limited to any specific combination of hardware circuitry and software.

In various embodiments, computer system 100 can be connected to one or more other computer systems, like computer system 100, across a network to form a networked system. The network can include a private network or a public network such as the Internet. In the networked system, one or more computer systems can store and serve the data to other computer systems. The one or more computer systems that store and serve the data can be referred to as servers or the cloud, in a cloud computing scenario. The other computer systems that send and receive data to and from the servers or the cloud can be referred to as client or cloud devices, for example.

The term "computer-readable medium" as used herein refers to any media that participates in providing instructions to processor 104 for execution. Such a medium may take many forms, including but not limited to, non-volatile media, volatile media, and transmission media. Non-volatile media includes, for example, optical or magnetic disks, such as storage device 110. Volatile media includes dynamic memory, such as memory 106. Transmission media includes coaxial cables, copper wire, and fiber optics, including the wires that comprise bus 102.

Common forms of computer-readable media or computer program products include, for example, a floppy disk, a flexible disk, hard disk, magnetic tape, or any other magnetic medium, a CD-ROM, digital video disc (DVD), a Blu-ray Disc, any other optical medium, a thumb drive, a memory card, a RAM, PROM, and EPROM, a FLASH-EPROM, any other memory chip or cartridge, or any other tangible medium from which a computer can read.

Various forms of computer readable media may be involved in carrying one or more sequences of one or more instructions to processor 104 for execution. For example, the instructions may initially be carried on the magnetic disk of a remote computer. The remote computer can load the instructions into its dynamic memory and send the instructions over a telephone line using a modem. A modem local to computer system 100 can receive the data on the telephone line and use an infra-red transmitter to convert the data to an infra-red signal. An infra-red detector coupled to bus 102 can receive the data carried in the infra-red signal and place the data on bus 102. Bus 102 carries the data to memory 106, from which processor 104 retrieves and executes the instructions. The instructions received by memory 106 may optionally be stored on storage device 110 either before or after execution by processor 104.

In accordance with various embodiments, instructions configured to be executed by a processor to perform a method are stored on a computer-readable medium. The computer-readable medium can be a device that stores digital information. For example, a computer-readable medium includes a compact disc read-only memory (CD-ROM) as is known in the art for storing software. The computer-readable medium is accessed by a processor suitable for executing instructions configured to be executed.

The following descriptions of various implementations of the present teachings have been presented for purposes of illustration and description. It is not exhaustive and does not limit the present teachings to the precise form disclosed. Modifications and variations are possible in light of the above teachings or may be acquired from practicing of the present teachings. Additionally, the described implementation includes software but the present teachings may be implemented as a combination of hardware and software or in hardware alone. The present teachings may be implemented with both object-oriented and non-object-oriented programming systems.

Subwaveform Detection of the P, Q, R, S, T, U, and J Waveforms

As described above, electrical signals flow through all the different muscle tissues of the heart. For the last 100 years conventional ECG devices have been able to detect some of these signals in the form of the P, Q, R, S, T, U, and J waveforms. These waveforms have aided in the diagnosis and treatment of many heart problems.

Unfortunately, however, the P, Q, R, S, T, U, and J waveforms do not provide a complete picture of the operation of all the different muscle tissues of the heart. As a result, improved systems and methods are needed to detect and analyze more information from the electrical signals that flow through all the different muscle tissues of the heart as it is beating. This additional information can be used to diagnose and treat many more heart problems.

In various embodiments, additional information is obtained from the electrical signals produced by a heart through signal processing. More specifically, signal processing is added to an ECG device in order to detect more information from the electrical signals that flow through all the different muscle tissues of the heart as it is beating.

Figure 7:
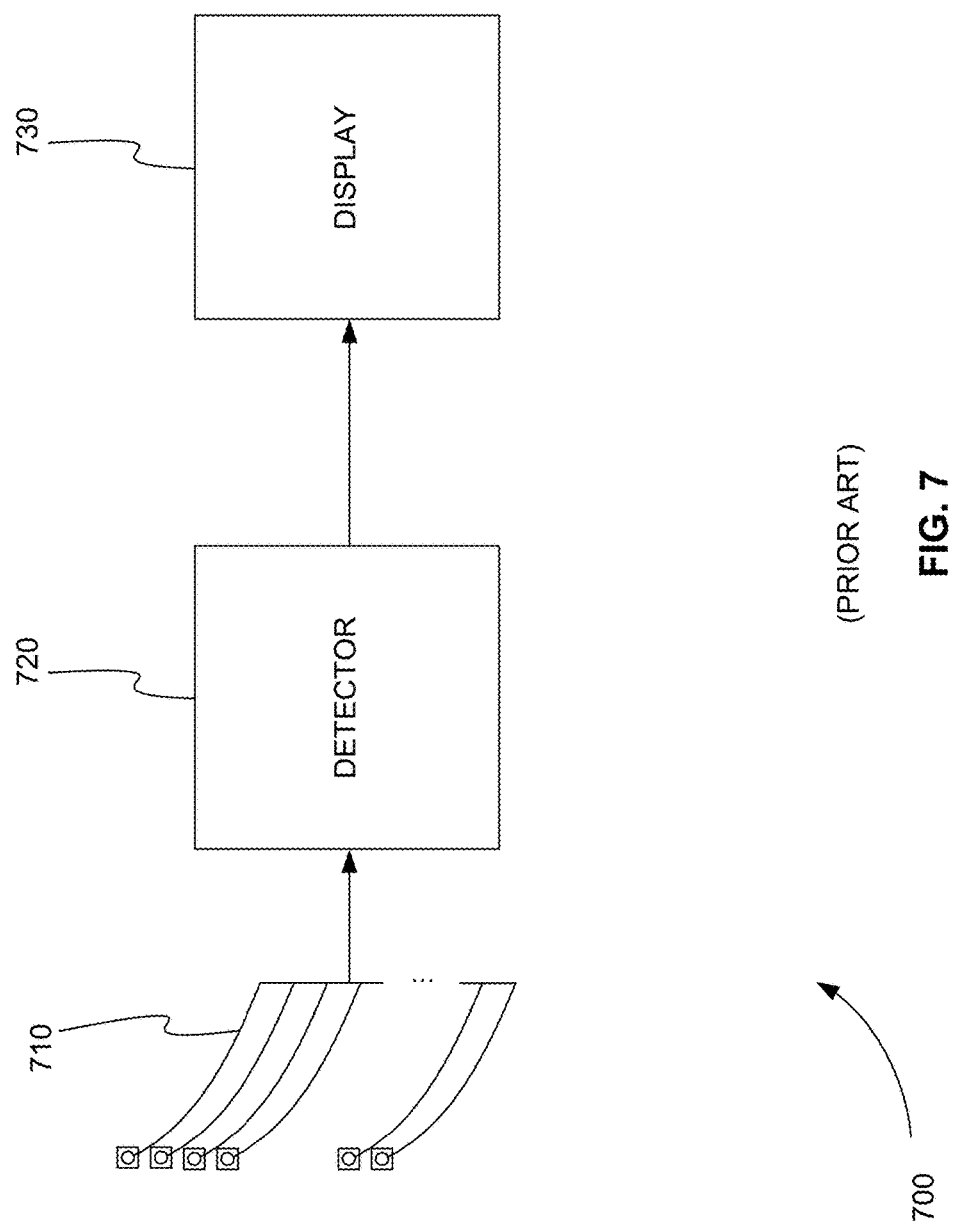
FIG. 7 is a block diagram of a conventional ECG device.

FIG. 7 is a block diagram 700 of a conventional ECG device. The conventional ECG device includes two or more leads or electrodes 710. Electrodes 710 are typically attached to the skin of a patient. Electrical signals produced by a beating heart are detected between pairs of electrodes 710. Because the heart is three-dimensional, electrodes are attached at different locations on a body to detect signals at different corresponding locations or angles from the heart. In other words, the electrodes are placed on a body to partially surround the heart. One typical type of ECG includes 12 electrodes, for example.

A voltage signal is detected between two electrodes 710 by detector 720. Detector 720 also typically amplifies the voltage signal. Detector 720 can also convert the voltage signal to a digital voltage signal using an analog to digital converter (A/D).

Detector 720 provides the detected and amplified voltage signal from each pair of electrodes 710 to display 730. Display 730 can be an electronic display device including, but not limited to, a cathode ray tube (CRT) device, light emitting diode (LED) device, or Liquid crystal display (LCD) device. Display 730 can also be a printer device. Additionally, display 730 can include a memory device to record detected signals. The memory device can be, but is not limited to, a volatile electronic memory, such as random access memory (RAM), a non-volatile electronic memory, such as electrically erasable programmable read-only memory (EEPROM or Flash memory), or a magnetic hard drive.

Figure 2:
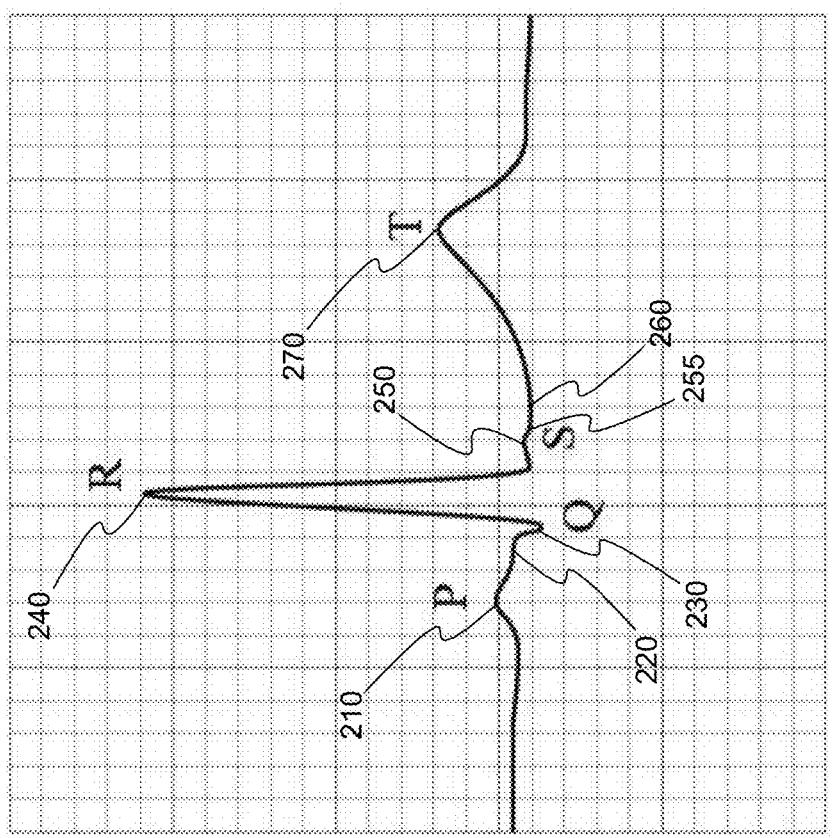
FIG. 2 is an exemplary plot of the P, Q, R, S, and T waveforms of a conventional electrocardiography (ECG) waveform of a heartbeat from a conventional ECG device.
Figure 3:
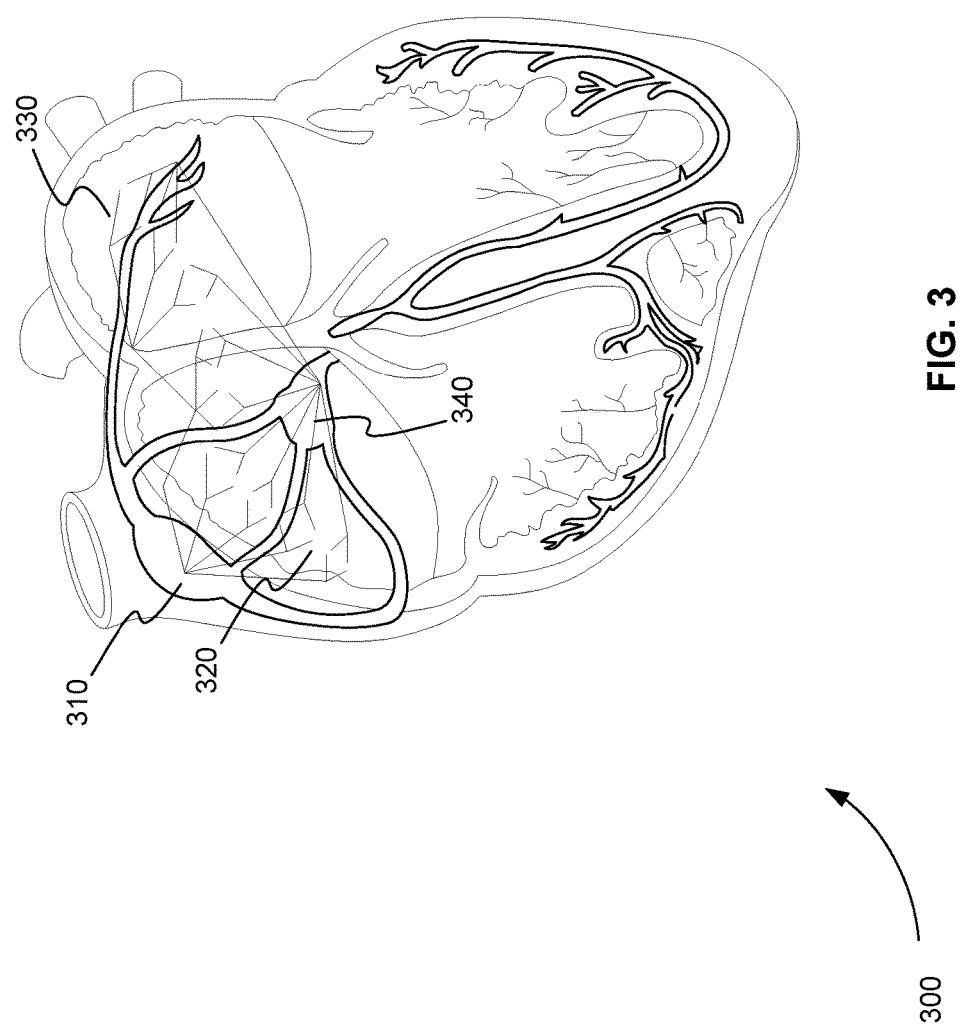
FIG. 3 is an exemplary diagram of the depolarization of the muscle tissue of a heart that produces the P waveform of FIG. 2 as detected by a conventional ECG device.
Figure 4:
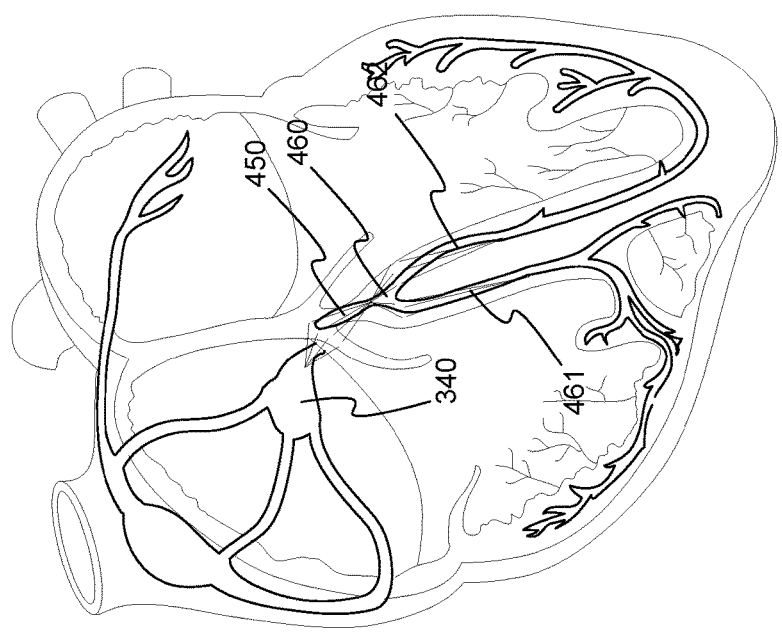
FIG. 4 is an exemplary diagram of the depolarization of the muscle tissue of a heart that produces the PR segment of FIG. 2 as detected by a conventional ECG device.
Figure 5:
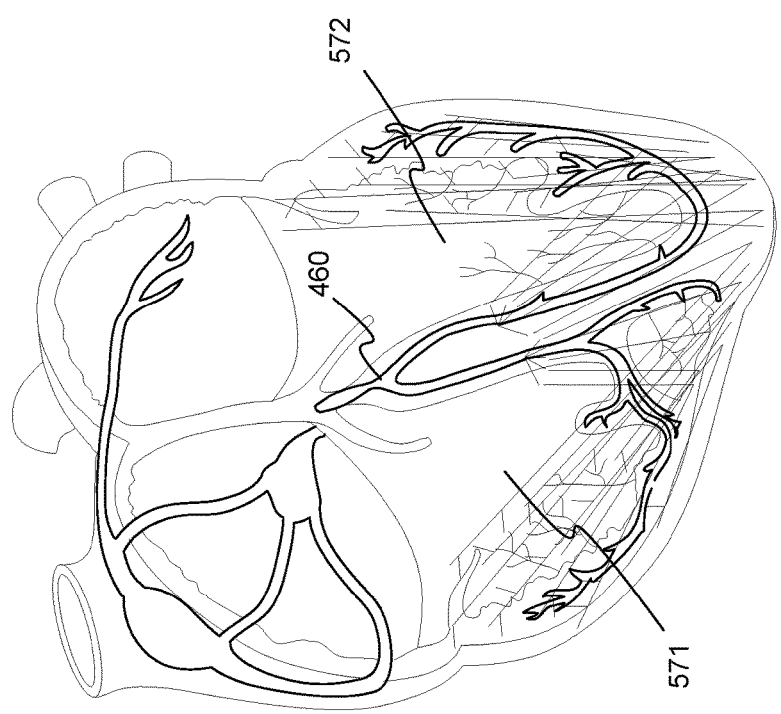
FIG. 5 is an exemplary diagram of the depolarization of the muscle tissue of a heart that produces the Q waveform, the R waveform, and the S waveform of FIG. 2 as detected by a conventional ECG device.
Figure 6:
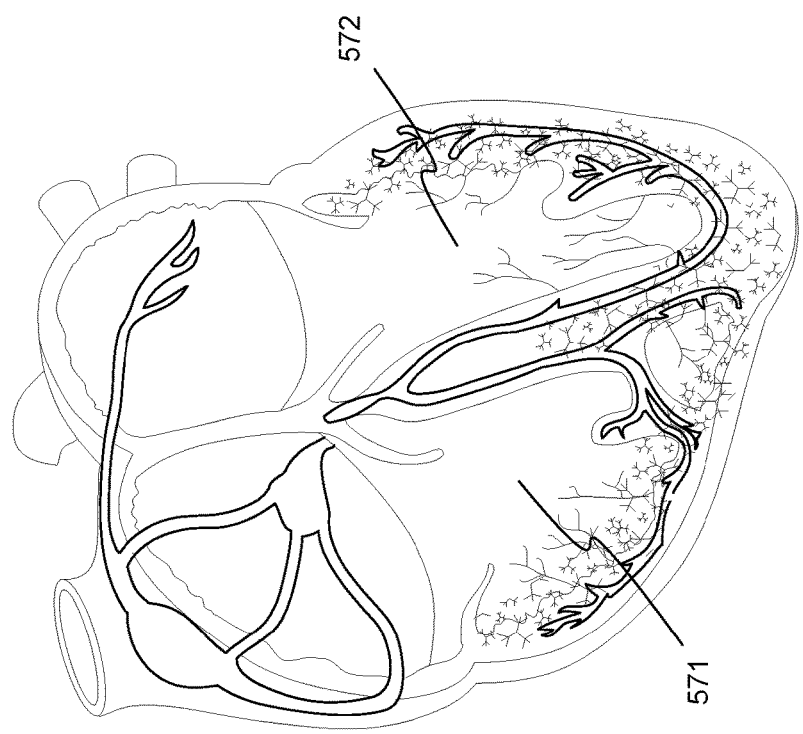
FIG. 6 is an exemplary diagram of the repolarization of the muscle tissue of a heart that produces the T waveform of FIG. 2 as detected by a conventional ECG device.

Display 730 displays a continuous loop of the detected P, Q, R, S, T, U, and J waveforms as shown in FIG. 2 for each pair of electrodes 710. Modern ECG devices can also include a processor (not shown), such as the processor shown in FIG. 1, to analyze the P, Q, R, S, T, U, and J waveforms. For example, the processor can calculate the time periods of the P, Q, R, S, T, U, and J waveforms and the times between the P, Q, R, S, T, U, and J waveforms. The processor can also compare this timing information to stored normal information. Based on the comparison, the processor can determine differences from the normal data. All information calculated by the processor can also be displayed on display 730.

Figure 8:
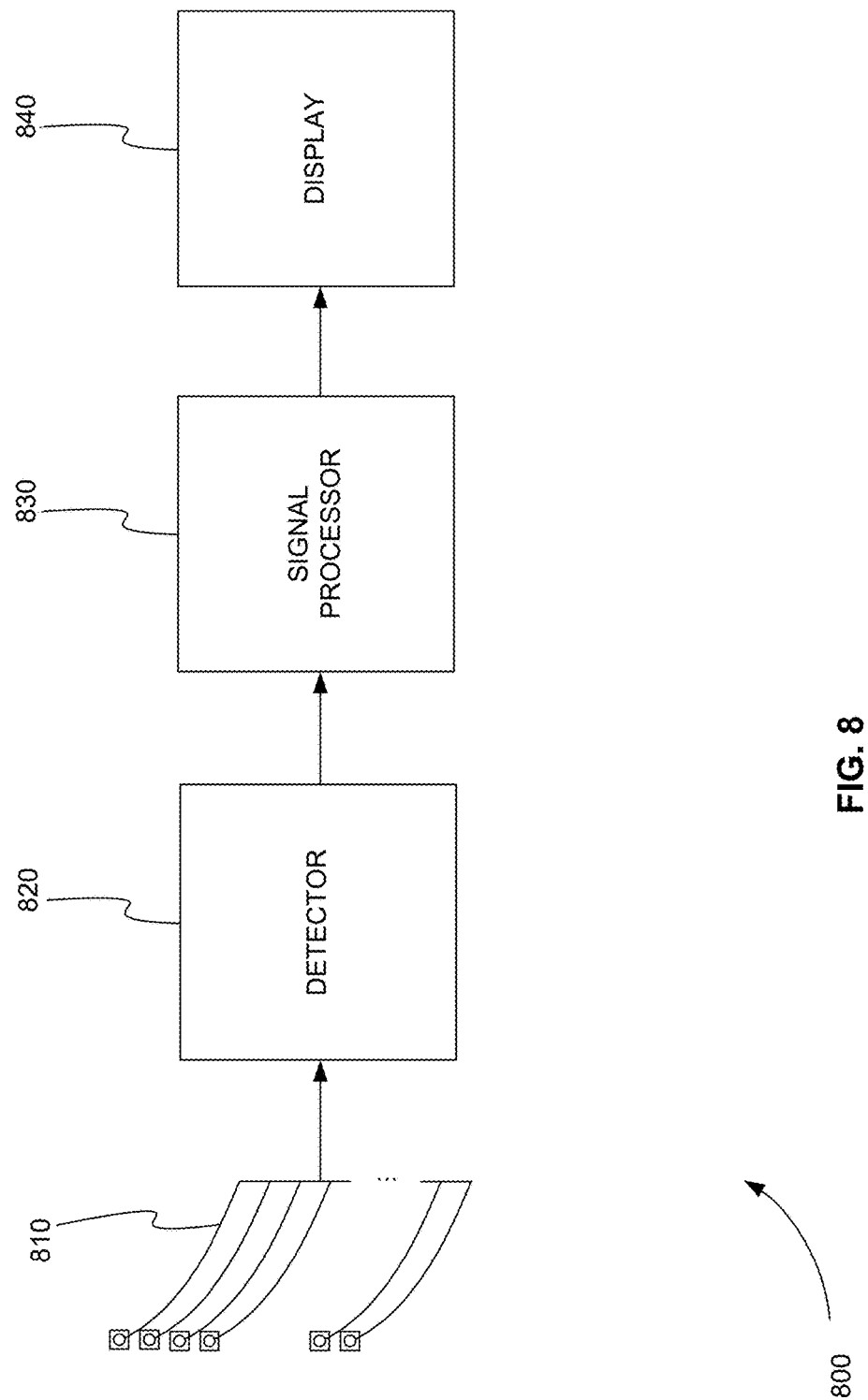
FIG. 8 is a block diagram of an ECG device for detecting more information from the electrical signals that flow through all the different muscle tissues of the heart as it is beating, in accordance with various embodiments.

FIG. 8 is a block diagram 800 of an ECG device for detecting more information from the electrical signals that flow through all the different muscle tissues of the heart as it is beating, in accordance with various embodiments. Electrodes 810 are attached to the skin of a patient, for example. Electrical signals produced by a beating heart are detected between pairs of electrodes 810.

A voltage signal is detected between two electrodes 810 by detector 820. Detector 820 also amplifies the voltage signal. Detector 820 also converts the voltage signal to a digital voltage signal using an analog to digital converter (A/D).

Detector 820 provides the detected and amplified voltage signal from each pair of electrodes 810 to signal processor 830. Detector 820 can also provide the detected and amplified voltage signal from each pair of electrodes 810 directly to display device 840 to display the conventional P, Q, R, S, T, U, and J waveforms.

Signal processor 830 detects or calculates one or more subwaveforms within and/or in the interval between the P, Q, R, S, T, U, and J waveforms of each detected and amplified voltage signal. A waveform is a shape or form of a signal. A subwaveform is shape or form of a signal that is within or part of another signal.

Signal processor 830 can be a separate electronic device that can include, but is not limited to, an application specific integrated circuit (ASIC), a field programmable gate array (FPGA), or a general purpose processor. Signal processor 830 can be software implemented on another processor of the ECG device, such as a processor of display device 840. Signal processor 830 can also be a remote server that receives the detected and amplified voltage signal from detector 820, detects or calculates one or more subwaveforms within and/or in the interval between the P, Q, R, S, T, U, and J waveforms, and sends the detected and amplified voltage signal and the one or more subwaveforms to display device 840.

Signal processor 830 sends one or more subwaveforms of each detected and amplified voltage signal to display device 840. Signal processor 830 can also calculate and send to the display device 840 the time periods of the one or more subwaveforms, the times between the one or more subwaveforms, and the times of the one or more subwaveforms in relation to the P, Q, R, S, T, U, and J waveforms and or the intervals between the P, Q, R, S, T, U, and J waveforms. Signal processor 830 can also compare this timing information to stored normal timing information. Based on the comparison, signal processor can determine differences from the normal data and send this difference information and any of the timing information to display device 840.

Display device 840 displays a continuous loop of the one or more subwaveforms for each pair of electrodes 810. Display device 840 can also display part or all of the conventional P, Q, R, S, T, U, and J waveforms for comparison with the one or more subwaveforms. Like display 730 of FIG. 7, display device 840 of FIG. 8 can be an electronic display device, a printer, or any combination of the two.

In various embodiments, an ECG device using signal processing to detect one or more subwaveforms within the P, Q, R, S, T, U, and J waveforms and/or within the intervals between the P, Q, R, S, T, U, and J waveforms is herein referred to as a saah ECG device. The voltage difference signals produced by a saah ECG device are referred to as saah ECG waveforms. The term "saah" is an acronym for some of the anatomically distinct portions of muscle tissue that produce subwaveforms. Specifically, saah stands for sinoatrial node (SAN), atria (right atrium (RA) and left atrium (LA)), atrioventricular node (AVN), and bundle of His (HIS). However, a saah ECG waveform is not limited to including subwaveforms representing the SAN, the atria, the AVN, and the HIS. A saah ECG waveform can include any subwaveform the P, Q, R, S, T, U, and J waveforms and/or within the intervals between the P, Q, R, S, T, U, and J waveforms.

Figure 9:
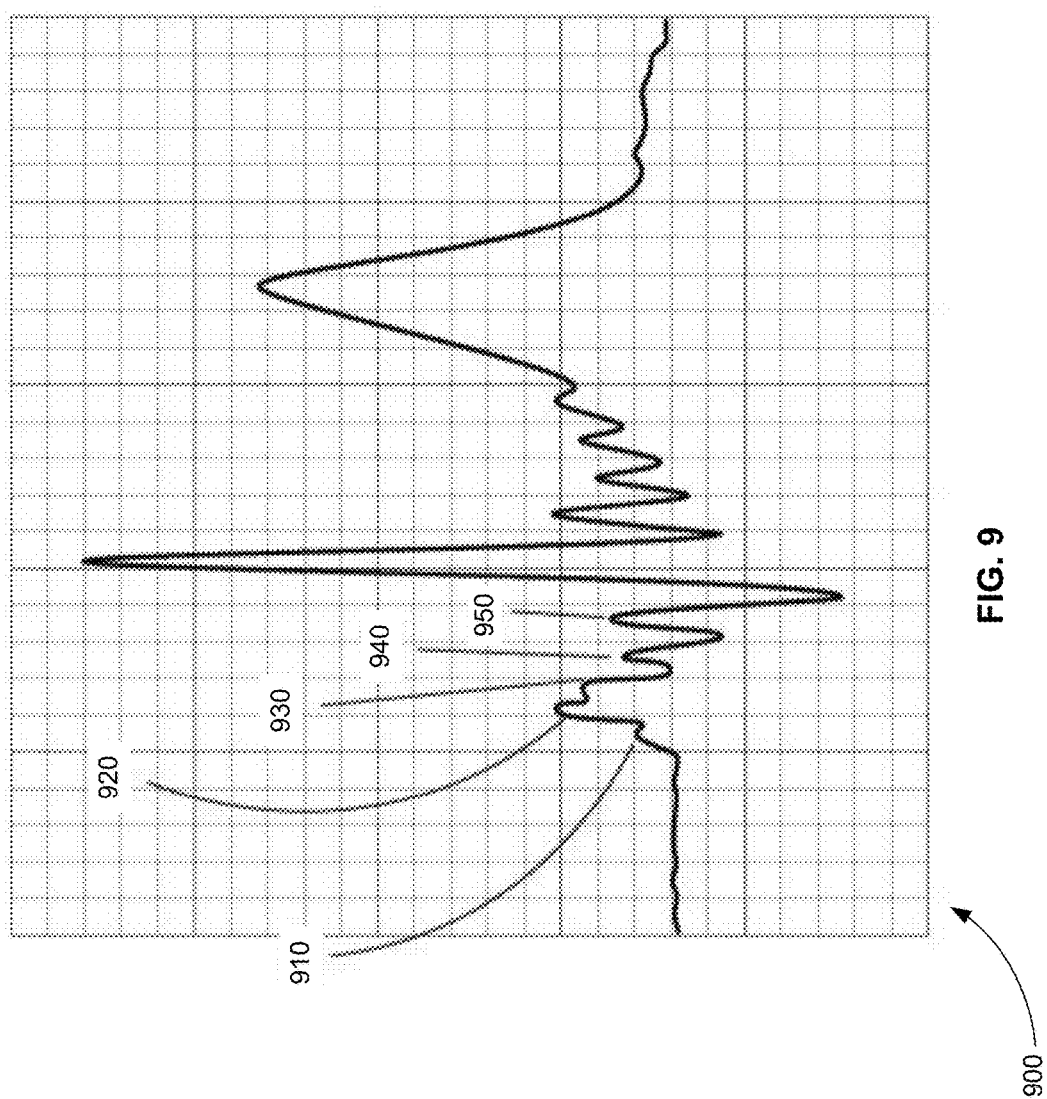
FIG. 9 is an exemplary plot of a saah ECG waveform of a heartbeat from a saah ECG device showing subwaveforms found within the P, Q, R, S, T, U, and J waveforms and/or within the intervals between the P, Q, R, S, T, U, and J waveforms, in accordance with various embodiments.

FIG. 9 is an exemplary plot 900 of a saah ECG waveform of a heartbeat from a saah ECG device showing subwaveforms found within the P, Q, R, S, T, U, and J waveforms and/or within the intervals between the P, Q, R, S, T, U, and J waveforms, in accordance with various embodiments. For example, five subwaveforms 910-950 of FIG. 9 are detected within the P waveform and the PR segment. The time period that includes the P waveform and the PR segment is also called the PR interval. Subwaveform 910 represents the depolarization of the SAN. Subwaveform 920 represents the depolarization of RA and LA. Subwaveform 930 represents the depolarization of the AVN. Subwaveform 940 represents the depolarization HIS. Finally, subwaveform 950 represents the depolarization of the bundle branches (BB).

In various embodiments, the subwaveforms of a saah ECG waveform are detected using signal processing. Electrodes 810 of the saah ECG of FIG. 8, for example, receive electrical impulses from anatomically distinct portions of muscle tissue or cells. The electrical impulses of anatomically distinct portions of muscle tissue of the heart have distinct frequencies. Through animal and human experimentation, the distinct frequency, frequency range, or frequency band of the anatomically distinct portions of muscle tissue of the heart are found. These distinct frequency bands of anatomically distinct portions of muscle tissue of the heart provide predetermined data or information for signal processing. In other words, the band pass frequency filtering of the signal processing is determined from the experimental data collected. A saah ECG device then employs one or more frequency band pass filters to detect the one or more subwaveforms.

Figure 10:
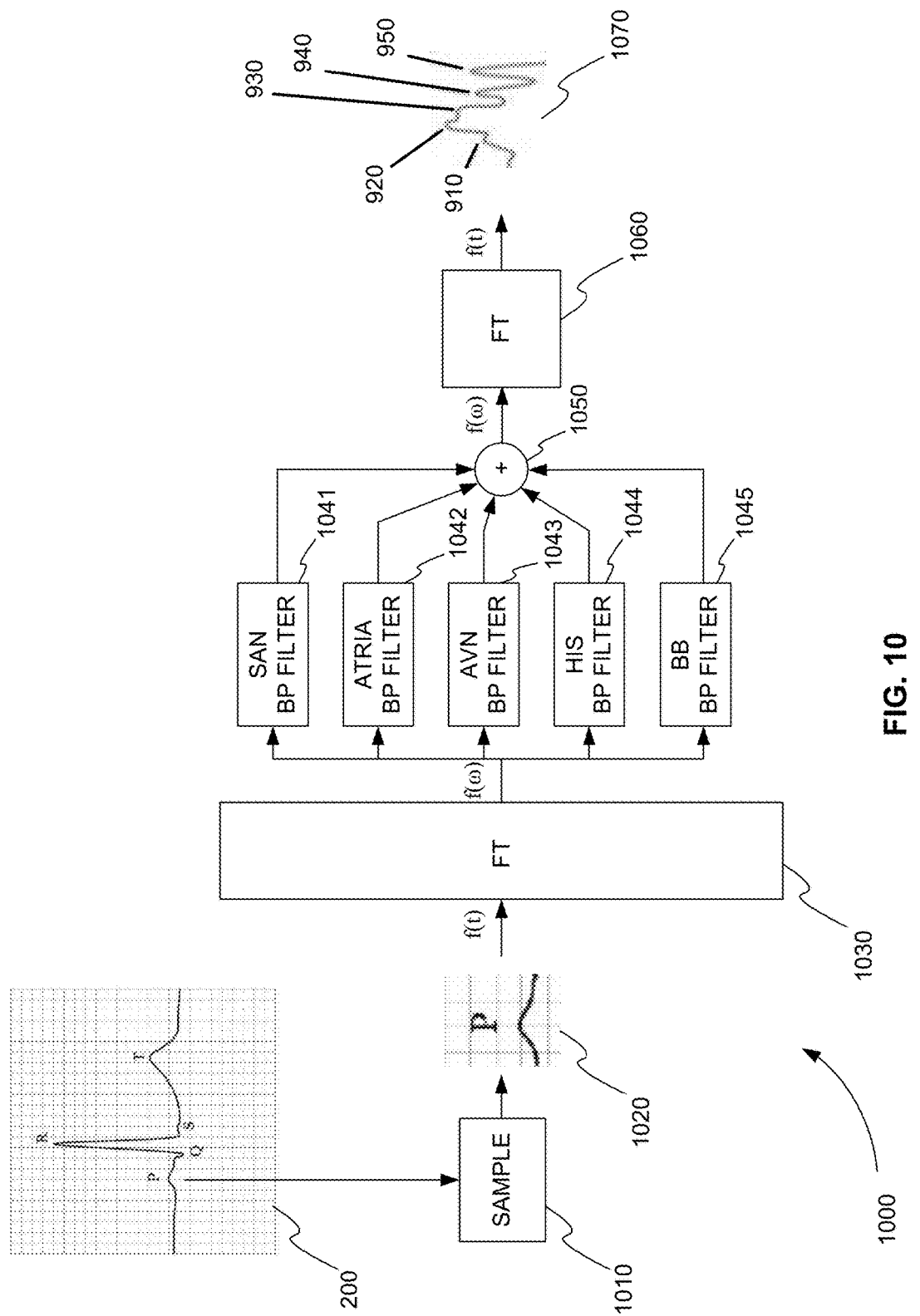
FIG. 10 is an exemplary block diagram showing a signal processing algorithm for detecting five subwaveforms within the PR interval of a conventional ECG waveform, in accordance with various embodiments.

FIG. 10 is an exemplary block diagram 1000 showing a signal processing algorithm for detecting five subwaveforms within the PR interval of a conventional ECG waveform, in accordance with various embodiments. Sampling block 1010 samples the electrical impulses in the PR interval time period of each heart. This is shown graphically in FIG. 1000 by separating PR interval 1020 from ECG waveform 200. The electrical impulses in the PR interval time period are sampled using electrodes 810 and detector 820 of FIG. 8, for example. Detector 820 of FIG. 8 can also amplify and convert the analog signal into a digital signal for digital processing.

The signal processing can be performed directly on the time domain signal received from a detector or the time domain signal received from a detector can be converted to the frequency domain for algorithmic processing. In FIG. 10, block 1030 converts the PR interval time domain signal to a PR interval frequency domain signal. The time domain signal is converted into a frequency domain signal using a Fourier transform, for example.

As described above, through animal and/or human experimentation, the frequency bands associated with depolarization of the SAN, atria, AVN, HIS, and BB of the heart are determined. Based on these frequency bands, band pass filters are created. Blocks 1041-1045 represent the band pass filters created to filter the PR interval frequency domain signal for frequency bands of the SAN, atria, AVN, HIS, and BB of the heart, respectively.

In block 1050, the frequency domain subwaveforms detected from the band pass filtering the frequency bands of the SAN, atria, AVN, HIS, and BB of the heart are summed. In block 1060, the filtered and summed frequency domain signal of the PR interval is converted back to a time domain signal. The frequency domain signal is converted into a time domain signal using a Fourier transform, for example.

The PR interval filtered and summed time domain signal 1070 includes five time domain subwaveforms 910-950. Subwaveforms 910-950 represent depolarization of the SAN, atria, AVN, HIS, and BB of the heart, respectively. Time domain signal 1070 can be used to replace PR interval 1020 in ECG waveform 200, for example. As a result, a saah ECG waveform is produced.

FIG. 10 shows a signal processing algorithm for detecting five subwaveforms. However, similar steps can be applied to detect fewer than five waveforms or more than five waveforms. Also, the steps of FIG. 10 describe detecting subwaveforms within the PR interval. However, similar steps can be applied to detect subwaveforms within the P, Q, R, S, T, U, and J waveforms and/or within one or more of the intervals between the P, Q, R, S, T, U, and J waveforms. In addition, the steps of FIG. 10 describe converting time signals to the frequency domain and then back to the time domain. One of ordinary skill in the art can appreciate that band pass filters can be applied directly to the time domain signal to provide the same result.

Figure 11:
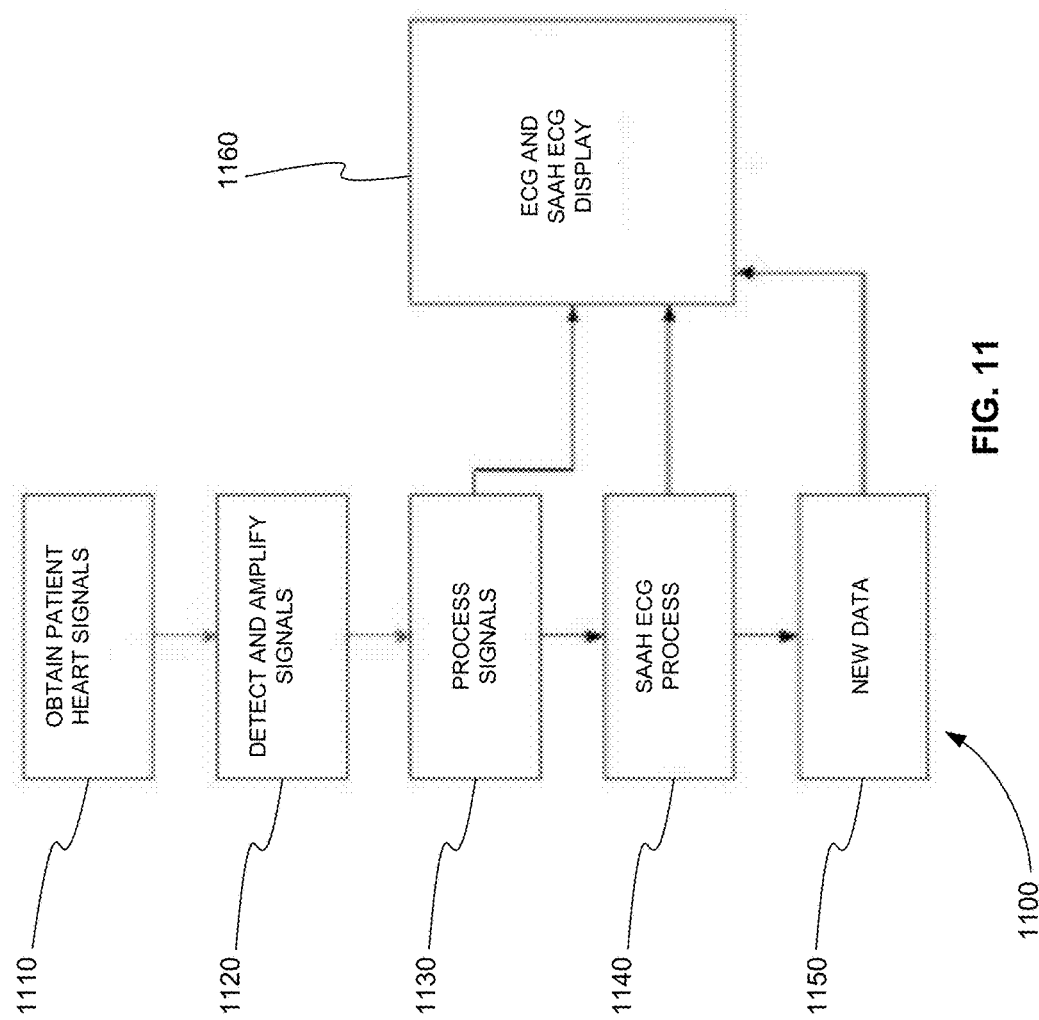
FIG. 11 is an exemplary block diagram of a saah ECG device that displays conventional ECG waveforms, saah ECG waveforms, and saah ECG data, in accordance with various embodiments.

FIG. 11 is an exemplary block diagram 1100 of a saah ECG device that displays conventional ECG waveforms, saah ECG waveforms, and saah ECG data, in accordance with various embodiments. In block 1110, patient heart signals are obtained. These heart signals can be obtained through noninvasive electrodes placed on the skin, such as electrodes 810 show in FIG. 8. In various embodiments, heart signals may also be obtained using invasive electrodes placed directly on the heart. In block 1120, the heart signals are detected using a detector and amplified.

In block 1130, the detected and amplified heart signals are processed using a signal processor. The signal processor detects the conventional P, Q, R, S, T, U, and J waveforms and sends them to the display of block 1160. The signal processor also detects or calculates subwaveforms within the conventional P, Q, R, S, T, U, and J waveforms and/or within intervals between the conventional P, Q, R, S, T, U, and J waveforms. The signal processor sends the subwaveforms to block 1140 for further processing. The processor of block 1140 produces the saah ECG waveform that includes the subwaveforms and sends the saah ECG waveform to the display of block 1160. The processor of block 1140 calculates additional information or new data from the saah ECG waveform. This new data can include, but is not limited to, timing information about the subwaveforms, timing information about the intervals between the subwaveforms, and timing information about the subwaveforms and their relation to the conventional P, Q, R, S, T, U, and J waveforms. In block 1150, this new data is sent to the display of block 1160.

The display of block 1160 displays a continuous loop of the conventional ECG waveform, the saah ECG waveform, and the new data from the subwaveforms. The display of block 1160 can display this information on an electronic display or print it on paper. The display of block 1160 can also record this information. The display of block 1160 can record this information on any type of memory device.

Figure 12:
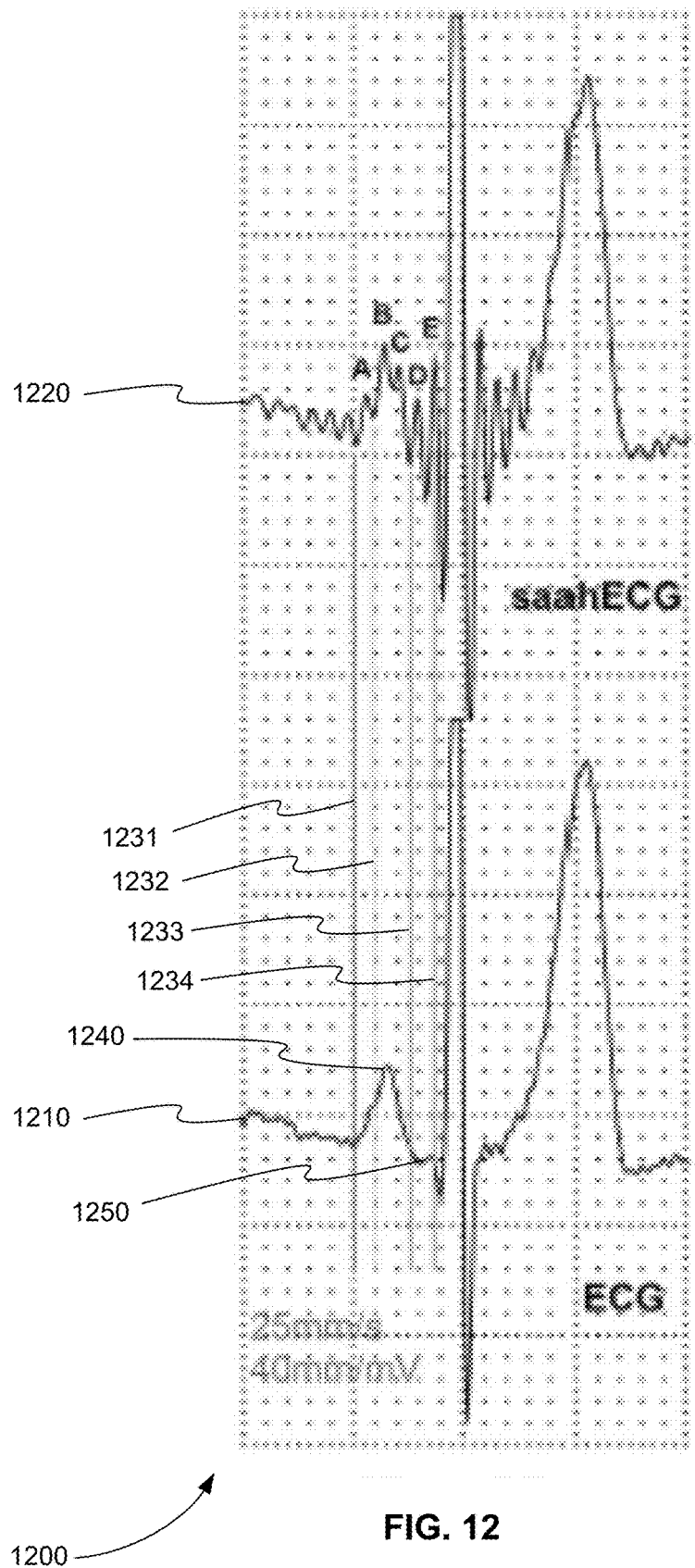
FIG. 12 is an exemplary plot of the information displayed by the saah ECG device of FIG. 10, in accordance with various embodiments.

FIG. 12 is an exemplary plot 1200 of the information displayed by the saah ECG device of FIG. 11, in accordance with various embodiments. Plot 1200 includes conventional ECG waveform 1210 and saah ECG waveform 1220. Saah ECG waveform 1220, for example, includes, among others, five subwaveforms A-E representing the depolarization of the SAN, the RA and LA, the AVN, the HIS, and the BB, respectively.

Plot 1200 also shows new data or timing information about the subwaveforms and their relation to the conventional P, Q, R, S, T, U, and J waveforms. For example, the time interval between line 1231 and line 1232 relates subwaveform A of saah ECG waveform 1220 to P waveform 1240 of conventional ECG waveform 1210. The time interval between line 1232 and line 1233 relates subwaveforms B and C of saah ECG waveform 1220 to P waveform 1240 conventional ECG waveform 1210. The time interval between line 1233 and line 1234 relates subwaveforms D and E of saah ECG waveform 1220 to PR segment 1250 conventional ECG waveform 1210.

Figure 13:
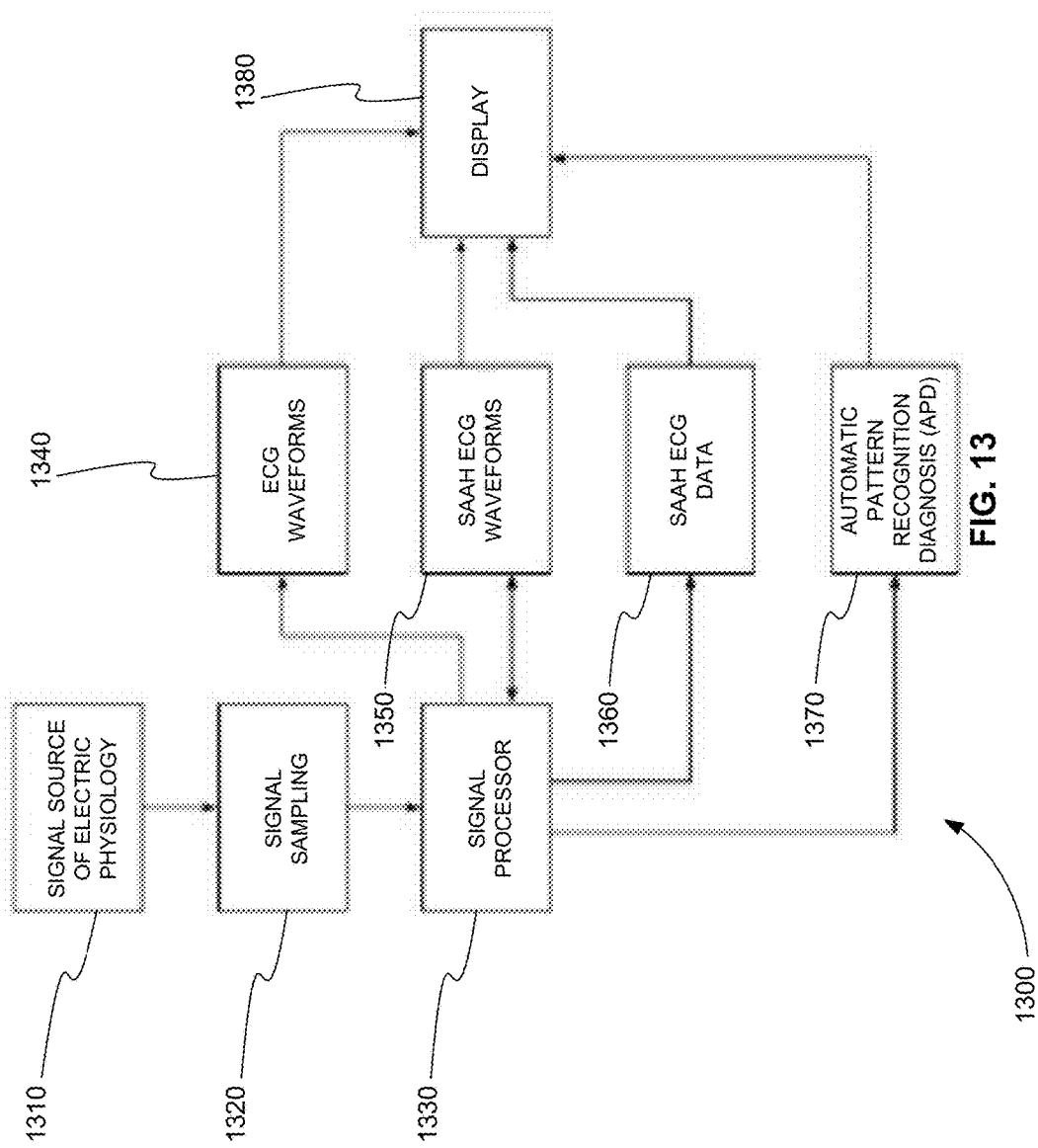
FIG. 13 is an exemplary block diagram of a saah ECG device that displays conventional ECG waveforms, saah ECG waveforms, saah ECG data, and saah ECG automatic pattern recognition diagnosis information, in accordance with various embodiments.

FIG. 13 is an exemplary block diagram 1300 of a saah ECG device that displays conventional ECG waveforms, saah ECG waveforms, saah ECG data, and saah ECG automatic pattern recognition diagnosis information, in accordance with various embodiments. In block 1310, patient heart signals are obtained. These heart signals can be obtained through noninvasive electrodes placed on the skin, such as electrodes 810 show in FIG. 8. In various embodiments, heart signals may also be obtained using invasive electrodes placed directly on the heart. In block 1320, the heart signals are sampled or detected using a detector. The heart signals may also be amplified.

In block 1330, the sampled heart signals are processed using a signal processor. The signal processor produces four different types of information from the sampled heart signals. As shown in block 1340, the signal processor produces conventional ECG waveforms including the conventional P, Q, R, S, T, U, and J waveforms and sends them to display 1380. As shown in block 1350, the signal processor produces saah ECG waveforms. These saah ECG waveforms include subwaveforms of the conventional P, Q, R, S, T, U, and J waveforms and the intervals between them. Note that the arrow between blocks 1330 and 1350 show information following in both directions. This shows that information from the saah ECG waveforms is further analyzed by the signal processor.

As shown in block 1360, the signal processor further analyzes the saah ECG waveforms to produce saah ECG data. This saah ECG data is sent to display 1380. Additionally, as shown in block 1370, the signal processor further analyzes the saah to obtain endocardium and epicardium data. This data is compared to recorded normal and abnormal data. The signal processor then produces automatic pattern recognition diagnosis (APD) information, and this information is sent to display 1380. APD information is, for example, patterns and/or colors that allows a user to easily and quickly determine that normal or abnormal endocardium and/or epicardium data was found.

Figure 14:
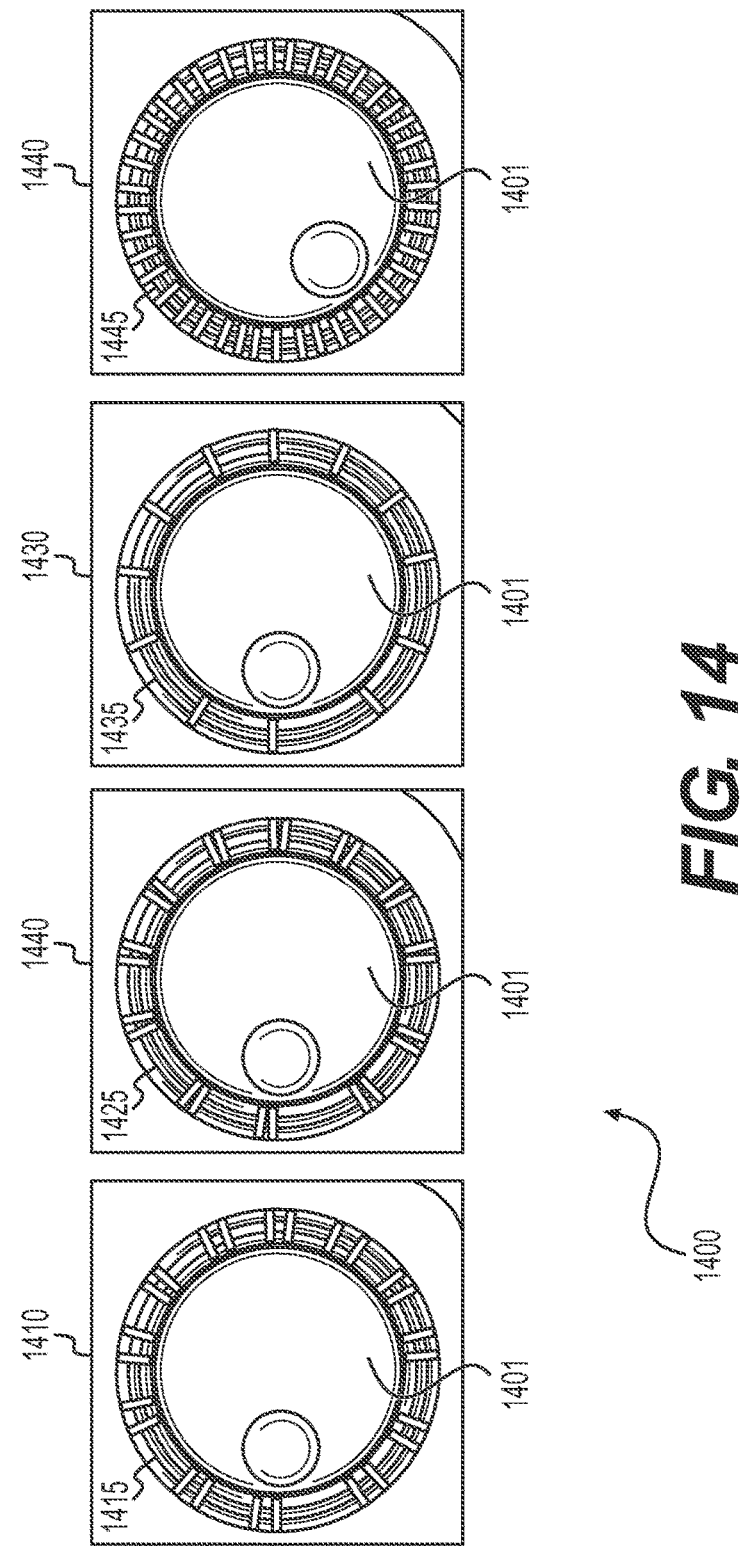
FIG. 14 is a series of photographs of automatic pattern recognition diagnosis (APD) information displayed around a rotating button of an exemplary saah ECG device, in accordance with various embodiments.

FIG. 14 is a series 1400 of photographs of automatic pattern recognition diagnosis (APD) information displayed around a rotating button of an exemplary saah ECG device, in accordance with various embodiments. Photograph 1410 shows information 1415 displayed around rotating button 1401. Information 1415 includes a pattern and colors that indicate a normal state of the saah ECG waveforms. Photograph 1420 shows information 1425 displayed around rotating button 1401. Information 1425 includes a pattern and colors that indicate a suspicious state of the saah ECG waveforms. Photograph 1430 shows information 1435 displayed around rotating button 1401. Information 1435 includes a pattern and colors that indicate an abnormal state of the saah ECG waveforms. Photograph 1440 shows information 1445 displayed around rotating button 1401. Information 1445 includes a pattern and colors that indicate an invalid result in the saah ECG waveforms.

In various embodiments, the additional information provided by a saah ECG device can be used to diagnose heart problems that cannot be diagnosed using conventional ECG devices or cannot easily be diagnosed using conventional ECG devices. The additional information provided by a saah ECG device can also be used in the treatment of heart problems or the assessment of these treatments.

Figure 15:
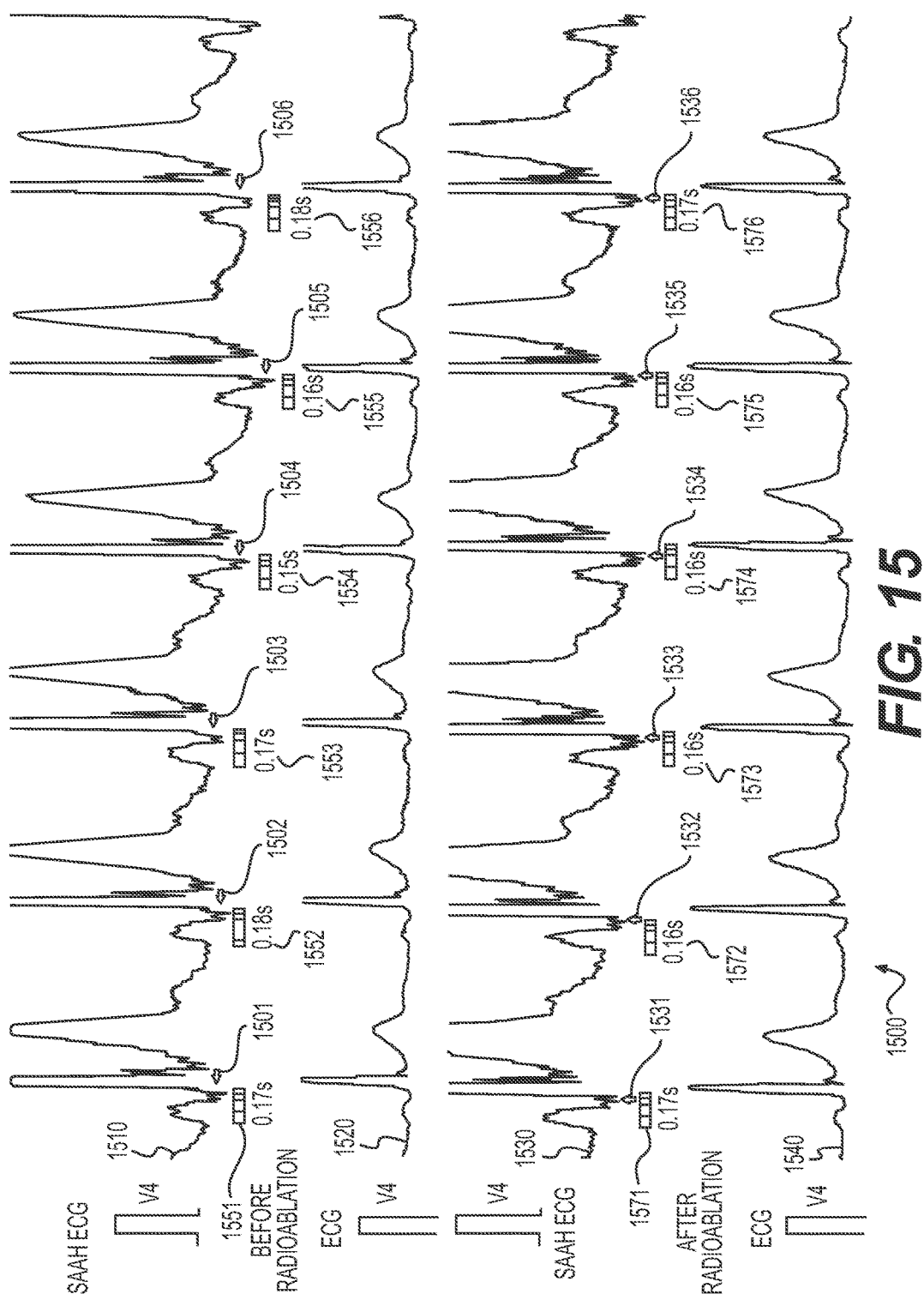
FIG. 15 is a plot of saah ECG and conventional ECG waveforms taken from a patient suffering from Wolff-Parkinson-White (WPW) syndrome before and after treatment with radiofrequency ablation (RFA) showing the additional diagnostic and treatment assessment information provided by a saah ECG device, in accordance with various embodiments.

FIG. 15 is a plot 1500 of saah ECG and conventional ECG waveforms taken from a patient suffering from Wolff-Parkinson-White (WPW) syndrome before and after treatment with radiofrequency ablation (RFA) showing the additional diagnostic and treatment assessment information provided by a saah ECG device, in accordance with various embodiments. WPW syndrome is caused by the presence of abnormal electrical pathways in the heart muscle tissue. There are, at least, three different types of abnormal pathways. These abnormal pathways cause cardiac tachycardia. Cardiac tachycardia is an abnormally rapid heart rate.

Plot 1500 shows before saah ECG waveform 1510, before conventional ECG waveform 1520, after saah ECG waveform 1530, and after conventional ECG waveform 1540. Waveforms 1510, 1520, 1530, and 1540 are produced for example using a saah ECG device. A saah ECG device also produces conventional ECG waveforms for comparison with the saah ECH waveforms. Waveforms 1510, 1520, 1530, and 1540 are produced using a $V_4$ electrode, for example. A $V_4$ electrode is placed in the fifth intercostal space (between ribs 5 and 6) in the mid-clavicular line, for example.

As described above, saah ECG waveforms show subwaveforms of the conventional P, Q, R, S, T, U, and J waveforms and the intervals between them. These subwaveforms provide more information on the function of specific and anatomically distinct portions of the muscle tissue of the heart.

For example, arrows 1503 and 1506 point to areas of two beats of before saah ECG waveform 1510 where the subwaveform showing the depolarization of the bundle branches (BB) is missing. Arrows 1501, 1502, 1504, and 1505 point to areas of four beats where the subwaveform showing the depolarization of the BB appears as half of the normal subwaveform. As a result, in two of the six beats of before ECG waveform 1510 the subwaveform representing the BB is missing, and in four of the six beats of before saah ECG waveform 1510 the subwaveform representing the BB is abnormal. A normal subwaveform representing the BB has a shape, for example, like subwaveform 950 of FIG. 9.

This information from before saah ECG waveform 1510 of FIG. 15 regarding the BB can be used to diagnose the specific abnormal pathway present in this case of WPW syndrome. Further this information can be used to determine the treatment. In contrast, none of this information can be obtained from before conventional ECG waveform 1520.

In addition to providing a saah ECG waveform, a saah ECG device can provide additional data regarding the subwaveforms found. For example, plot 1500 includes subwaveform timing information for the PR interval of each heartbeat. This timing information is provided as timing diagrams 1551-1556 for the six heartbeats. Each timing diagram provides a numeral value for the period of the PR interval and a horizontal stacked bar graph depicting how four time intervals containing one or more subwaveforms are distributed with PR interval time period. The horizontal stacked bar graphs can include different colors, patterns, or shades, for example.

The first interval of each horizontal stacked bar graph is the interval that includes the subwaveform representing the depolarization of the sinoatrial node (SAN). The second interval is the interval that includes the subwaveforms representing the depolarization of the atria (right atrium (RA) and left atrium (LA)) and the atrioventricular node (AVN). The third interval is the interval that includes the subwaveform representing the depolarization of the bundle of His (HIS) of the beating heart. The fourth interval is the interval that includes the subwaveform representing the depolarization of the bundle branches (BB).

A comparison of the horizontal stacked bar graphs of timing diagrams 1551-1556 shows that the periods of the four intervals vary widely over the six heartbeats. This is also an indication of the underlying disease. This timing information is not available in before conventional ECG waveform 1520.

RFA was performed on the patient presenting before saah ECG waveform 1510 and before conventional ECG waveform 1520. A muscular conduction bridge connecting the right atrium and the right ventricle (bundle of Kent) and a connections between the A-V bundle and the interventricular septum (Mahaim's connections) were ablated, for example.

After treatment with RFA, the patient's return to a normal heartbeat can be confirmed with after saah ECG waveform 1530. For example, arrows 1531-1536 of the six heartbeats shown in after saah ECG waveform 1530 point to areas that show that the subwaveform of the BB has returned in all six heartbeats after treatment. In contrast, after conventional ECG waveform 1540 cannot provide this information.

In addition, a comparison of the horizontal stacked bar graphs of timing diagrams 1571-1576 for after saah ECG waveform 1530 shows that the periods of the four intervals of the PR interval do not vary widely over the six heartbeats. This is also an indication of the effectiveness of the RFA treatment. This timing information is not available in after conventional ECG waveform 1540.

System for Detecting ECG Subwaveforms

In various embodiments, an electrocardiography (ECG) system for detecting one or more subwaveforms within the P, Q, R, S, T, U, and J waveforms or in an interval between the P, Q, R, S, T, U, and J waveforms is provided. Returning to FIG. 8, the ECG system includes two or more electrodes 810, a detector 820, a signal processor 830, and a display device 840.

Two or more electrodes 810 are placed proximate to a beating heart that receive electrical impulses from the beating heart. Two or more electrodes 810 are shown in FIG. 8 as noninvasive electrodes that are attached to the skin of a patient. In various embodiments, two or more electrodes 810 can be invasive electrodes placed directly on or within heart tissue.

Detector 820 is electrically connected to two or more electrodes 810. Detector 820 detects the electrical impulses from at least one pair of electrodes of the two or more electrodes 810. Detector 820 converts the electrical impulses to an ECG waveform for each heartbeat of the beating heart. Detector 820, for example, samples the electrical impulses. In various embodiments, detector 820 further amplifies the ECG waveform. In various embodiments, detector 820 further performs analog to digital (A/D) conversion on the ECG waveform. In various embodiments, detector 820 provides an ECG waveform with a higher signal-to-noise (S/N) ratio than conventional ECG devices.

Signal processor 830 is electrically connected to detector 820. Signal processor receives the ECG waveform from detector 820. Signal processor 830 detects or calculates one or more subwaveforms within P, Q, R, S, T, U, and J waveforms of the ECG waveform or in an interval between the P, Q, R, S, T, U, and J waveforms that represent the depolarization or repolarization of anatomically distinct portions of muscle tissue of the beating heart. Signal processor 830 produces a processed ECG waveform that includes the one or more subwaveforms for each heartbeat.

Signal processor 830 can be a separate device, can be software running on device of detector 820 or display device 840, or can be software running on a remote server and communicating with detector 820 and display device 840 through one or more communication devices. Signal processor 830 can be a separate device that includes, but is not limited to, an application specific integrated circuit (ASIC) or a field programmable gate array (FPGA) or a general purpose processor. A general purpose processor can include, but is not limited to, a microprocessor, a micro controller, or a computer such as the system shown in FIG. 1. Signal processor 830 can be software implemented on another processor of the ECG device, such as a processor of display device 840. Signal processor 830 can also be a remote server that receives the detected and amplified difference voltage signal from detector 820, detects or calculates one or more subwaveforms within and/or in the interval between the P, Q, R, S, T, U, and J waveforms, and sends the detected and amplified different voltage signal and the one or more subwaveforms to display device 840.

Display device 840 receives the processed ECG waveform for each heartbeat and displays the processed ECG waveform for each heartbeat. The processed ECG waveform is called a saah ECG waveform, for example. As described above, display device 840 can be an electronic display device including, but not limited to, a cathode ray tube (CRT) device, light emitting diode (LED) device, or Liquid crystal display (LCD) device. Display device 840 can also be a printer device or any combination of an electronic display device and a printer. Additionally, display device 840 can include a memory device to record saah ECG waveforms, saah ECG data and conventional ECG waveforms and data. The memory device can be, but is not limited to, a volatile electronic memory, such as random access memory (RAM), a non-volatile electronic memory, such as electrically erasable programmable read-only memory (EEPROM or Flash memory), or a magnetic hard drive.

In various embodiments, the detected one or more subwaveforms include at least one subwaveform representing depolarization of the sinoatrial node (SAN), the atria (right atrium (RA) and left atrium (LA)), the atrioventricular node (AVN), the bundle of His (HIS), or the bundle branches (BB) of the beating heart.

In various embodiments, the display device 840 further displays the ECG waveform for comparison with the processed ECG waveform.

In various embodiments, signal processor 830 further calculates timing information about the one or more subwaveforms, timing information about the intervals between the one or more subwaveforms, and timing information about the one or more subwaveforms and their relation to the P, Q, R, S, T, U, and J waveforms of the ECG waveform for each heartbeat. Display device 840 further receives this timing information from signal processor 830. Display device 840 displays the timing information about the one or more subwaveforms, the timing information about the intervals between the one or more subwaveforms, and the timing information about the one or more subwaveforms and their relation to the P, Q, R, S, T, U, and J waveforms of the ECG waveform for each heartbeat.

In various embodiments the ECG system further includes a memory device (not shown). The memory device receives the ECG waveform and the processed ECG waveform from the signal processor.

In various embodiments, the memory device further includes normal processed ECG waveform data. Normal processed ECG waveform data is stored on the memory device using signal processor 830 or a general purpose processor (not shown). Signal processor 830 further compares the processed ECG waveform to the normal processed ECG waveform data and calculates a status condition based on the comparison. The status conditions are, for example, normal, suspicious, or abnormal.

In various embodiments, the ECG system includes a second display device (not shown) surrounding a rotating button (not shown). Signal processor 830 further sends a colored pattern to the second display device based on the status condition. The second display device provides automatic pattern recognition diagnosis (APD).

Method for Detecting ECG Subwaveforms

Figure 16:
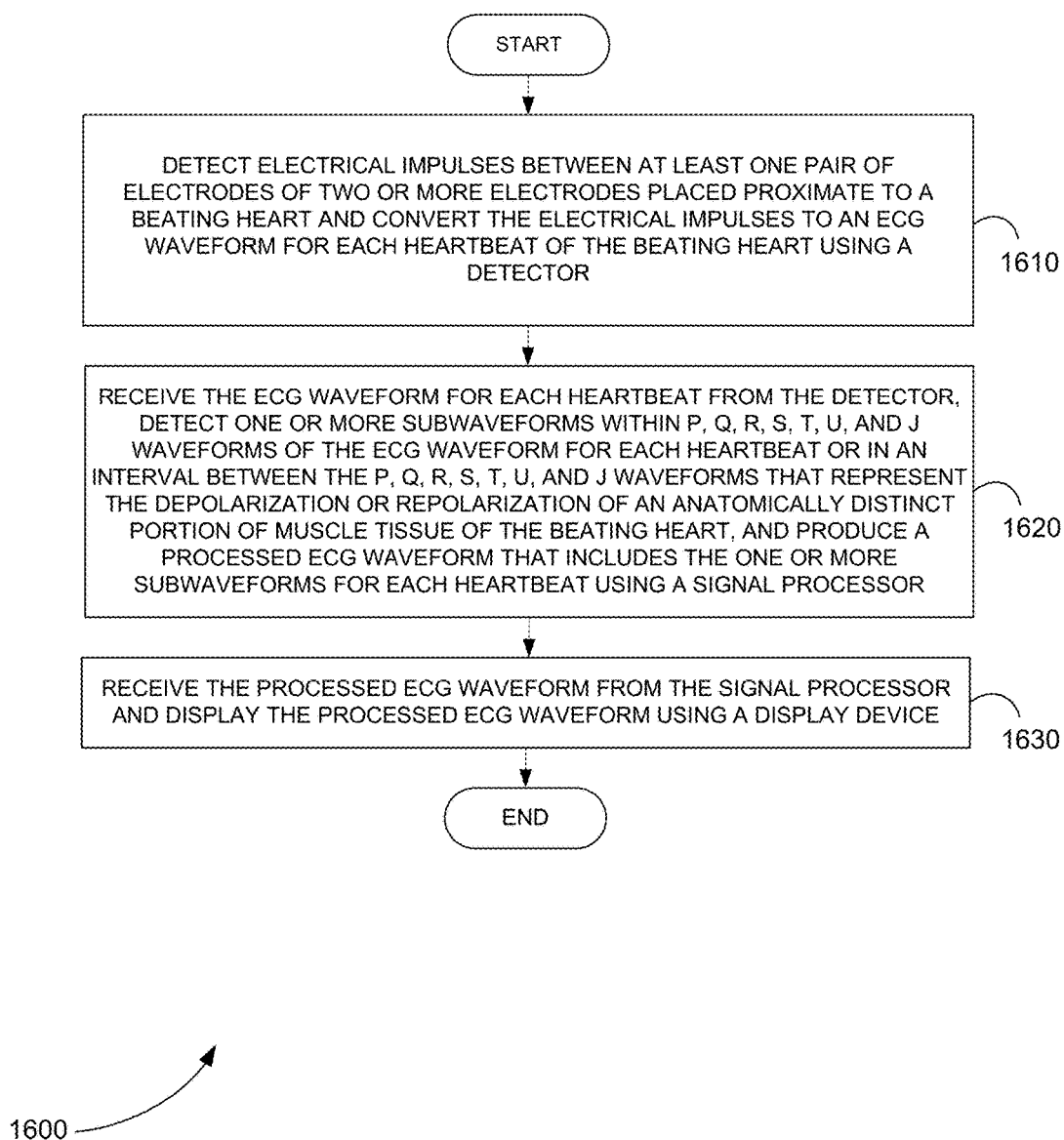
FIG. 16 is a flowchart showing a method for detecting subwaveforms within the P, Q, R, S, T, U, and J waveforms of an ECG waveform of a heartbeat or in an interval between the P, Q, R, S, T, U, and J waveforms, in accordance with various embodiments.

FIG. 16 is a flowchart showing a method 1600 for detecting subwaveforms within the P, Q, R, S, T, U, and J waveforms of an ECG waveform of a heartbeat or in an interval between the P, Q, R, S, T, U, and J waveforms, in accordance with various embodiments.

In step 1610 of method 1600, electrical impulses are detected between at least one pair of electrodes of two or more electrodes placed proximate to a beating heart using a detector. The electrical impulses are converted to an ECG waveform for each heartbeat of the beating heart using the detector.

In step 1620, the ECG waveform for each heartbeat is received from the detector using a signal processor. One or more subwaveforms within P, Q, R, S, T, U, and J waveforms of the ECG waveform for each heartbeat or in an interval between the P, Q, R, S, T, U, and J waveforms that represent the depolarization or repolarization of an anatomically distinct portion of muscle tissue of the beating heart are detected using the signal processor. A processed ECG waveform that includes the one or more subwaveforms for each heartbeat is produced using the signal processor.

In step 1630, the processed ECG waveform is received from the signal processor and the processed ECG waveform is displayed using a display device.

Computer Program Product for Detecting ECG Subwaveforms

In various embodiments, computer program products include a tangible computer-readable storage medium whose contents include a program with instructions being executed on a processor so as to perform a method for detecting subwaveforms within the P, Q, R, S, T, U, and J waveforms of an ECG waveform of a heartbeat or in an interval between the P, Q, R, S, T, U, and J waveforms. This method is performed by a system that includes one or more distinct software modules.

Figure 17:
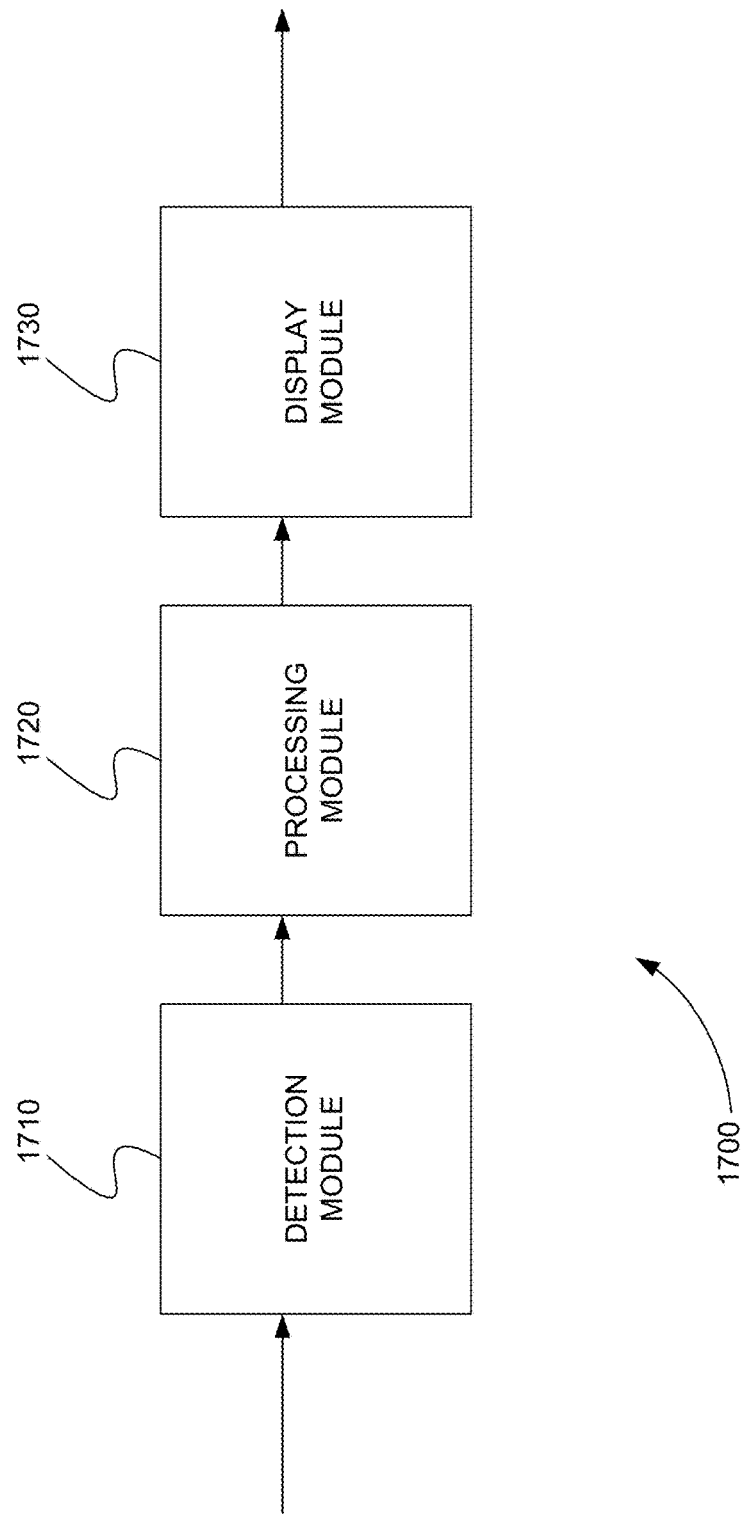
FIG. 17 is a schematic diagram of a system that includes one or more distinct software modules that performs a method for detecting subwaveforms within the P, Q, R, S, T, U, and J waveforms of an ECG waveform of a heartbeat or in an interval between the P, Q, R, S, T, U, and J waveforms, in accordance with various embodiments.

FIG. 17 is a schematic diagram of a system 1700 that includes one or more distinct software modules that performs a method for detecting subwaveforms within the P, Q, R, S, T, U, and J waveforms of an ECG waveform of a heartbeat or in an interval between the P, Q, R, S, T, U, and J waveforms, in accordance with various embodiments. System 1700 includes detection module 1710, processing module 1720, and display module 1730.

Detection module 1710 detects electrical impulses between at least one pair of electrodes of two or more electrodes placed proximate to a beating heart. Detection module 1710 converts the electrical impulses to an ECG waveform for each heartbeat of the beating heart.

Processing module 1720 receives the ECG waveform for each heartbeat. Processing module 1720 detects one or more subwaveforms within P, Q, R, S, T, U, and J waveforms of the ECG waveform for each heartbeat or in an interval between the P, Q, R, S, T, U, and J waveforms that represent the depolarization or repolarization of an anatomically distinct portion of muscle tissue of the beating heart. Processing module 1720 produces a processed ECG waveform that includes the one or more subwaveforms for each heartbeat.

Display module 1730 receives the processed ECG waveform. Display module 1730 displays the processed ECG waveform.

Cardiomyocyte Conduction Speed Mapping

The heart muscle, like other muscles, is activated by biologically generated electrical signals. Electrocardiography (ECG or EKG) has long been used to measure and record these electrical signals. Essentially, in ECG the electrical activity of the heart is measured from a number of different points on the body and plotted over time. As a result, ECG traces out each cardiac cycle or heartbeat as a voltage versus time waveform.

A human heart has two functional systems. The first system, referred to as a self-conduction system, is part of the atrium (including left and right atria). In a traditional ECG, the self-conduction system is represented by the P wave or PR interval. The excitation, rhythm and conduction of every beat is completed by the collaboration of all parts of the heart, which is an axis system, including: sinoatrial node (SAN)-atrial-atrioventricular node (AVN)-Bundle of His-Bundle Branches (left and right). The Bundle of His is a collection of heart muscle cells specialized for electrical conduction that transmits the electrical impulses from the AVN to the point of the apex of the fascicular branches. Complex arrhythmias disease typically occurs in these different areas. However, ECG is only half of a sine wave.

The second system, referred to as a cardiac work system, is a pump system (one for each complete contraction and relaxation of the heart), which is done by the heart muscles. The main part of the second system is the left ventricle. In the traditional ECG, it is represented by the T wave or QT interval. There are about 10 million ventricular myocardial cells, without nerves or tracts.

Features or waves of each heartbeat waveform have been known for more than a century to correspond to electrical signals activating various parts of the heart. For example, the P wave is known to result from an electrical signal directed from the SAN to the AV node activating the atrium of the heart, to the Bundle of His to the left and right Bundle Branches, and the T wave is known to result from a recovery electrical signal (ventricular depolarization and repolarization) sent to the ventricles of the heart after they have contracted. As a result, physicians are able to diagnose specific heart problems by analyzing the shapes and time of these waves.

It is thought that an ECG heartbeat waveform includes much more information about the anatomy of the heart that is not being used (scanning and displaying). In particular, it is thought that at least some of the waves in an ECG heartbeat waveform include subwaveforms that provide more detailed information about parts of the heart, as described above. Consequently, there is a need for systems and methods of processing biological electrical signals, such as signals read by ECG, in order to provide additional information about anatomical structures.

ECG has been used in the clinic for more than 100 years to trace P, Q, R, S, T, U, and J waveforms, generating measurements such as P-R, Q-R, Q-T, S-T, etc. These are waveforms for which data is measured and plotted over time on the x-axis. However, traditional ECG does not provide any detailed discrete data for specific anatomical regions of the P, Q, R, S, T, U, and J waveforms. Specifically, the generated P-wave and T-wave both are half sine waves. The whole T wave band has included the entire ventricular myocyte and 10 layers of myocardium conduction. Of the displayed myocardial information, only ST-T can be measured in terms of time (i.e., transit duration), although the data information is too sparse.

Electrocardiogram is a form of morphology, requiring clinical experience to read ECG, because every doctor's interpretation of waveform change is different. For most medical practitioners, the electrocardiogram poses many challenges to doctors because of the length of clinical experience required.

The most significant clinical problem of ventricular myocyte ECG is that with existing ECG it is impossible to be measured and read at the ventricular T wave band, when the T wave disappears or is lost, flattened, or inverted. Secondly, in complex cases, if the T wave is buried in P waves or buried in QRS, ECG cannot be read. Thirdly, in existing ECG, there is a significant problem of the diagnosis rate of ischemia, MI, AMI, ACS and CAD being low. For example, presently, the diagnostic accuracy rate is only 20-25%. Fourthly, existing ECG is unable to assess the heart's pumping capacity or the HF. Fifthly, existing ECG cannot assess whether arrhythmia will result in myocardial damage or injury, or the degree of damage degree. Sixthly, existing ECG cannot assess efficacy before and after surgery and before and after drug administration, and thus invasive methods cannot be performed.

In various embodiments, methods and systems convert the first one third of subwaveforms of the T waveform into discrete data. The changes are then calculated in cell conduction time between myocardium layers and in space, using lead systems and transverse and frontal plane positioning. The results can be accurate to the $26^{th}$ decimal point, which cannot be achieved by the conventional linear ECG. Since there are no conduction bundles within the more than 100 million cells making up the ventricular myocyte, the conduction between cardiomyocyte depends on intercalated discs and gap transmission. The exchange between endocardial (inside) and epicardial (outside) cells has regular rhythms, which in turn sets the rhythm at which the heart beats, and is the key part forming the functional heart system.

In various embodiments, subwaveforms in the electrocardiogram T waveform morphology and composition, myocardial structure, cardiomyocyte conduction velocity, etc. are supplemented with discrete data. Such discrete data enables doctors to read the electrocardiogram in the traditional manner, while also comparing the discrete data with ECG pattern. In other words, the original T waveform electrocardiogram, which is hard to understand, irregular, extremely variable, and essentially similar from person to person, is supplemented with precise digitized or discrete data. In terms of identifying characteristic features and patterns for each patient, supplementing the morphologic waveform with discrete data enables doctors to conduct more precise assessment, measurement, analysis, judgment, and diagnosis.

Digital Cardiomyocytes Conduction Speed Mapping

In various embodiments, after 12-lead cardio bioelectric signals have been collected, and after subwaveform signal processing has been performed, as described above, methods and system utilize nonlinear mathematical theory using special signal processing methods to convert the biological electrocardiogram into specific discrete data. Such conversion is done according to the theory of the 12-lead ECG system, on the basis of directivity and time sequencing, and utilizing transverse and frontal plane positioning.

Figure 18:
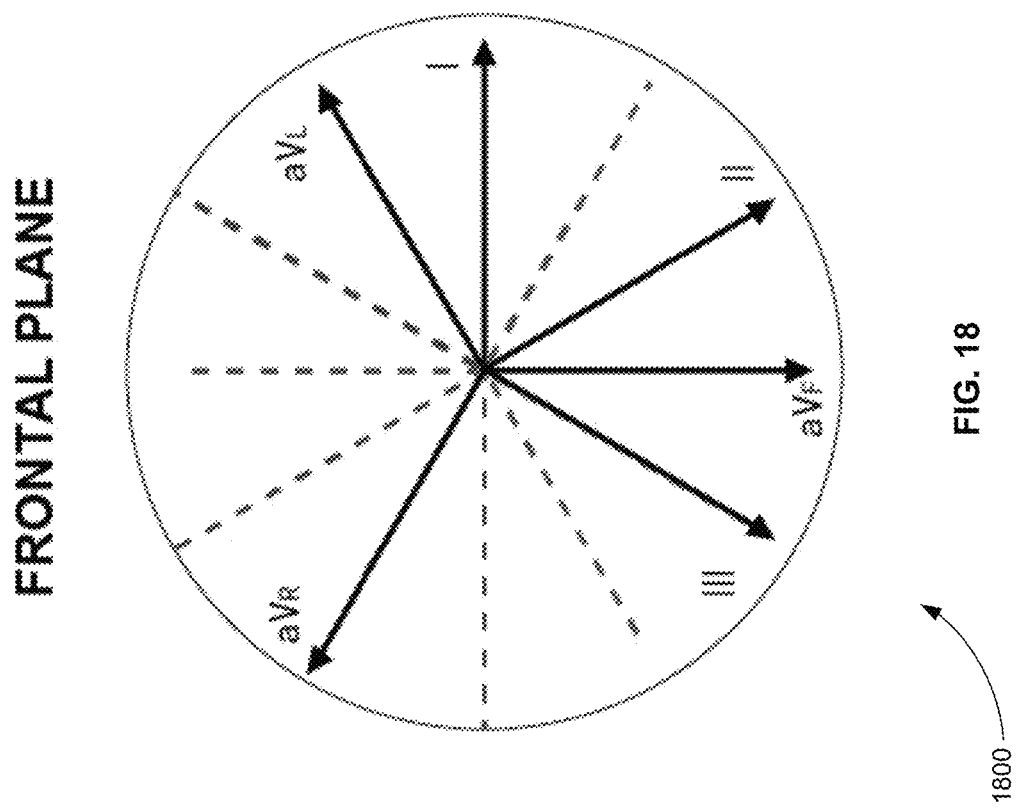
FIG. 18 is an exemplary diagram showing the positioning of leads $aV_R$, $aV_L$, I, II, $aV_F$, and III in the frontal plane, in accordance with various embodiments.

FIG. 18 is an exemplary diagram 1800 showing the positioning of leads $aV_R$, $aV_L$, I, II, $aV_F$, and III in the frontal plane, in accordance with various embodiments.

Figure 19:
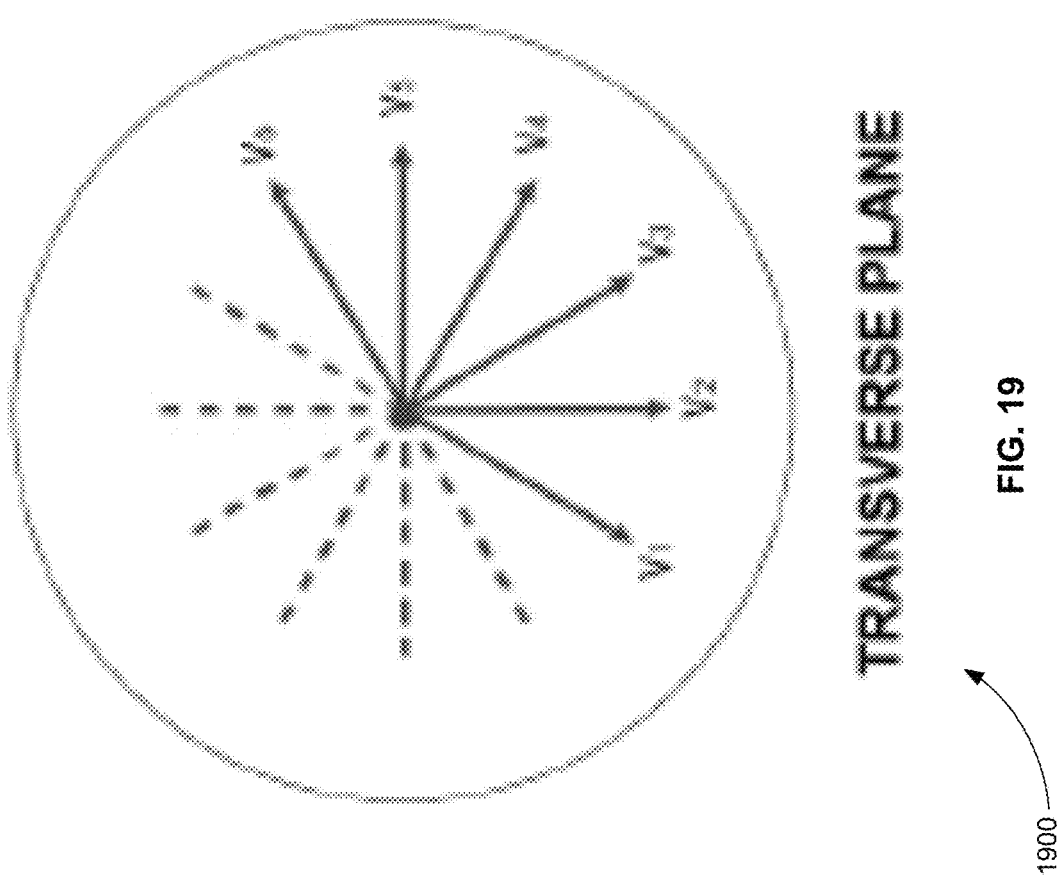
FIG. 19 is an exemplary diagram showing the positioning of leads $V_1$, $V_2$, $V_3$, $V_4$, $V_5$, and $V_6$ in the transverse plane, in accordance with various embodiments.

FIG. 19 is an exemplary diagram 1900 showing the positioning of leads $V_1$, $V_2$, $V_3$, $V_4$, $V_5$, and $V_6$ in the transverse plane, in accordance with various embodiments.

Figure 20:
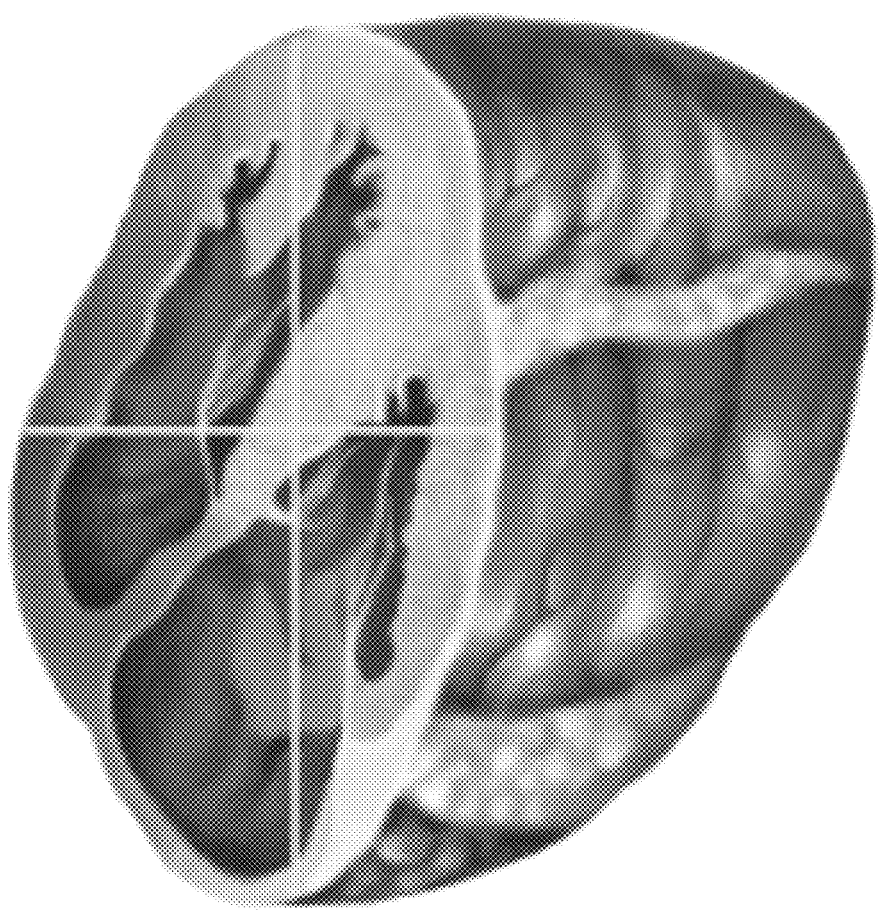
FIG. 20 is an exemplary diagram showing the myocardium space orientation, in accordance with various embodiments.

FIG. 20 is an exemplary diagram 2000 showing the myocardium space orientation, in accordance with various embodiments.

Figure 21:
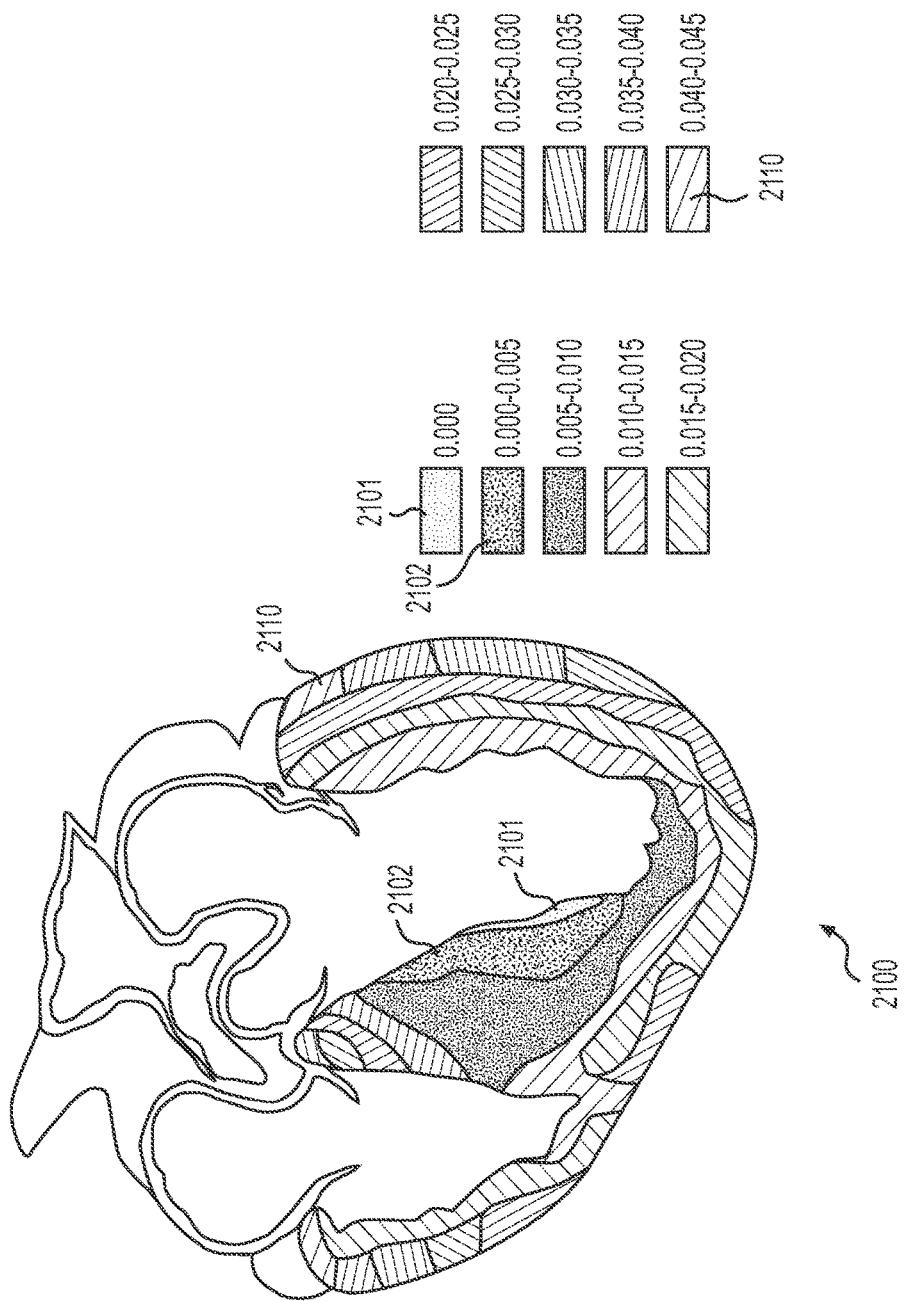
FIG. 21 is an exemplary cross sectional diagram showing ten layers of the myocardium and their conduction sequence and times, in accordance with various embodiments.

FIG. 21 is an exemplary cross sectional diagram 2100 showing ten layers of the myocardium and their conduction sequence and times, in accordance with various embodiments. For example, conduction or repolarization begins in layer 2101 of the ventricle at time 0.000 s, and propagates to layer 2102 at a time between time 0.000 and 0.005 s. Conduction moves through the next seven layers until ending in layer 2010 at a time between 0.040 and 0.045 s. These are the times for a normal heart, for example.

Figure 22:
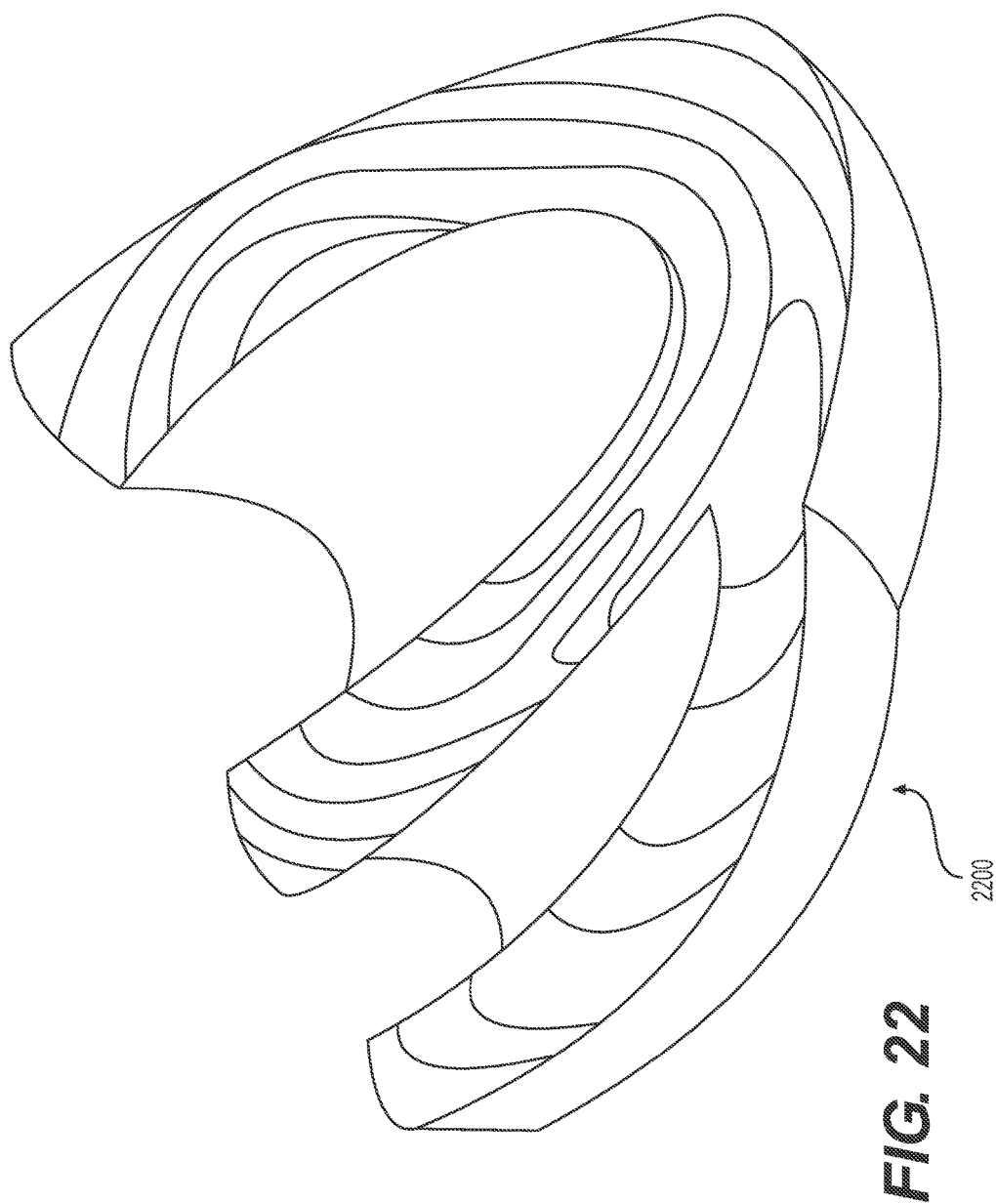
FIG. 22 is an exemplary cross sectional diagram showing the stratification of the ventricular layers, accordance with various embodiments.

FIG. 22 is an exemplary cross sectional diagram 2200 showing the stratification of the ventricular layers, accordance with various embodiments.

In various embodiments, the method of operating the ECG is the same as with conventional 12-lead ECG. In other words, after signal processing, frequency division, and dimension division, the data is mapped according to the heart frontal plane and transverse plane—the origin position of each anatomical region, the frequency, distance, direction, and size at their various positions (time and distance) are displayed naturally. This is the principle of cardiac electrophysiological conduction, and also the cardiac conduction rhythm system.

Application in Diagnosis on the Basis of Clinical Physiopathological and Electrophysiological Theory Cardiomyocyte characteristics are as follows. The characteristic of the action potential of cardiomyocyte production by the ventricular conduction system (ventricle) is known as excitability. The cells of the heart conduction system (atrium) can spontaneously produce cardiac action potential, which is known as automaticity, and the characteristic of the cardiomyocyte in the ventricle to regularly contract is known as rhythm. When the cardiomyocyte becomes excited, depolarization and repolarization occur to produce action potential (AP). The negative potential value of the resting membranes of working cells in the heart is substantial, the depolarization velocity is rapid, showing rapid responses to electrical activities. In certain pathological cases (such as myocardial ischemia, hypoxia, drug intoxication), the membrane potential decreases (the negative value decreases), making rapid response cells show slow response to electrical activity.

If there are pathological changes in the tissue of the myocardial layers (ischemia, effusion, necrosis, stunning and the like), it may result in changes in voltage and current resistance. This is determined by the cardiomyocyte characteristics themselves. This rule cannot be altered. If the cell shows slow response to electrical activity, this represents an abnormal signal. In various embodiments, the theoretical basis of the systems and methods is designed according to such electrophysiological theory.

This is the first instance of digital replacement of waveforms for ventricular cardiomyocyte conduction time, using digital measurement to more precisely analyze ventricular myocyte. This can effectively be applied in, for example, the accurate assessment of disease, positioning, judgment, identification and diagnosis, choosing drug therapeutic regimens, choosing surgical regimens, and emergency rapid diagnosis. It can be non-invasive and safe, it reduces costs, and it uses the same test methods as the traditional ECG. Perhaps more importantly, it can explore heart theories and discover new theories, and also be applied to various medical instruments.

Transmission of the Cardiac Impulse in the Ventricular Muscle

Once the impulse reaches the ends of the Purkinje fibers, it is transmitted through the ventricular muscle mass by the ventricular muscle fibers themselves. The velocity of transmission is now only 0.3 to 0.5 m/sec, one sixth that in the Purkinje fibers. The cardiac muscle wraps around the heart in a double spiral, with fibrous septa between the spiraling layers. Therefore, the cardiac impulse does not necessarily travel directly outward toward the surface of the heart but instead angulates toward the surface along the directions of the spirals. Because of this, transmission from the endocardial surface (inside) to the epicardial surface (outside) of the ventricle requires as much as another 0.03 second, approximately equal to the time required for transmission through the entire ventricular portion of the Purkinje system. Thus, the total time for transmission of the cardiac impulse from the initial bundle branches to the last of the ventricular muscle fibers in the normal heart is about 0.06 second.

Clinical Application Value

Because traditional electrocardiograms only display half sine waves for the T-wave band, the changes that occur with vascular heart disease are not obvious. Also, ECG begins to change only after myocardial ischemia reaches 70%. After ischemia in acute myocardial infarction (AMI), acute coronary syndrome (ACS), coronary artery disease (CAD), the proportion of ECGs that do not change is amazing. There are a significant number of documents and research reports worldwide. Among ECG waveforms, the T-wave band contains immeasurable cardiomyocyte information. Generally, with early phase and intermediate phase pathological changes, there are some changes in ST-T, such as: flattening, disappearing, deformation, and position shifts, but they cannot be diagnosed in clinic. Only when the disease is very serious, such as with AMI or ACS, is the T-wave inverted, and the ST-segment raised or lowered. For many patients, especially males from 40-65 years old, namely very serious patients, their ECG is not changed at all, because the male heart beat is very strong, and the male cardiac output is greater than the female output.

The anatomical structure of heart ventricular myocyte is composed of endocardial cells, M cells, and epicardial cells. In total, more than 100 million cells constitute the myocardial wall. The structure of the ventricular myocyte is composed of 10 layers, with electrical activity coming from the septum, in an up and down and left and right direction, conducted in 360 degrees.

In various embodiments, when the electrocardiogram's ST-T has not changed, or has not obviously changed, the clinical ECG cannot be definitively diagnosed and assessed. Such a technical advantage can be valuable. When the diseased location of AMI/CAD is very small and the ECG has not changed, the data may be larger than normal by 3-5× or larger, making the digitalization very obvious.

In various embodiments, in each heartbeat, there are 10 data values (time values) for each lead (10 myocardial layers). There are 120 data values in total for 12 leads, with an additional 12 mean values from 12 leads. The normal and abnormal state can be identified according to normal myocardial electrophysiological potential.

Displaying each heartbeat of the ten myocardial layers follows a regular procedure. The excitation time of each myocardial layer, along with the color and pattern of the myocardial layer excited is displayed. If one lead has abnormal data, the whole lead will have abnormal value, and the pathological change of a certain layer can also be analyzed. The mapping of spatial scope is analyzed using digital table. Each myocardial layer is indicated by a column of the table, using different colors and different patterns, for example. The rows of the table are the 12 leads of the ECG, for example.

FIG. 23 is an exemplary table 2300 showing the timing values for 10 layers of the ventricle recorded at 12 different leads of an ECG for a 35 year-old normal male, in accordance with various embodiments. The 10 columns of table 2300 represent the 10 muscle layers of the ventricle. The 12 rows of table 2300 represent the 12 different leads of the ECG. Each cell of table 2300 includes the time of conduction measured for the particular layer and lead. Note that table 2300 represents just one heartbeat.

Figure 24:
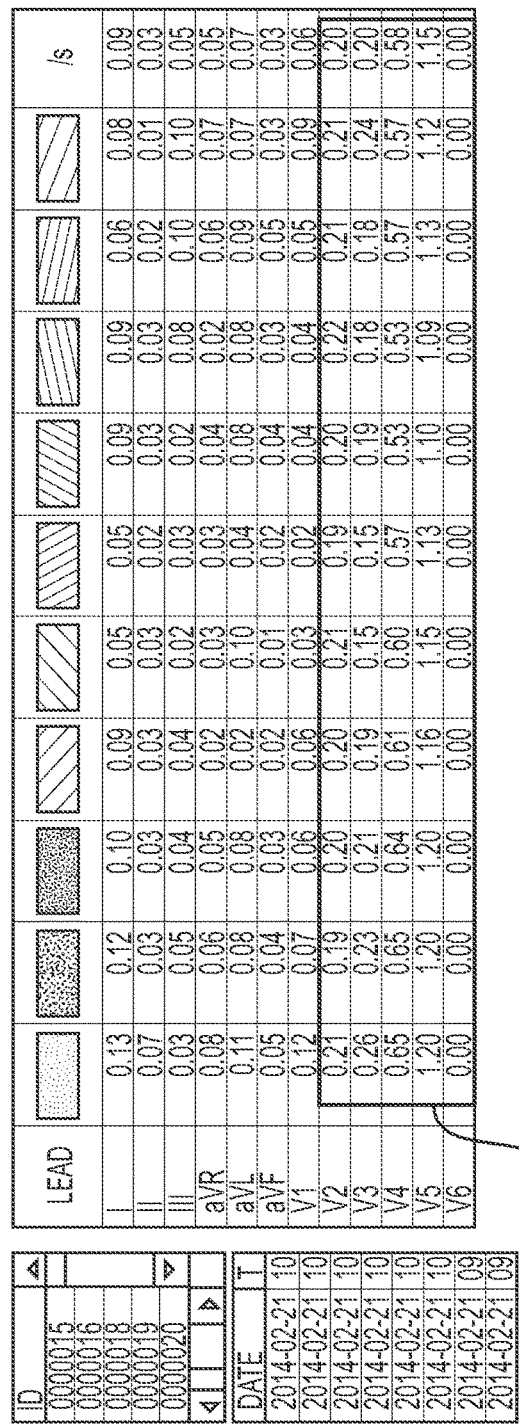
FIG. 24 is an exemplary table showing the timing values for 10 layers of the ventricle recorded at 12 different leads of an ECG for a 51 year-old male before intervention who has a left anterior descending artery with 80% proximal, 90% middle, and 70% distal blockage, in accordance with various embodiments.

FIG. 24 is an exemplary table 2400 showing the timing values for 10 layers of the ventricle recorded at 12 different leads of an ECG for a 51 year-old male before intervention who has a left anterior descending artery with 80% proximal, 90% middle, and 70% distal blockage, in accordance with various embodiments. The abnormal data caused by the blockage is shown in box 2410 of table 2400.

FIG. 25 is an exemplary table 2500 showing the timing values for 10 layers of the ventricle recorded at 12 different leads of an ECG for a 51 year-old male after percutaneous coronary intervention (PCI, formerly known as angioplasty with stent) who had a left anterior descending artery with 80% proximal, 90% middle, and 70% distal blockage, in accordance with various embodiments. Note that a comparison of FIGS. 24 and 25 shows that abnormal data shown in box 2410 of table 2400 is back to normal in FIG. 25. This confirms that the timing data of the layers of the ventricle recorded at leads of an ECG is able to detect myocardial problems, such as blockages.

System for Digitizing Conduction Information

In various embodiments, an electrocardiography (ECG) system for detecting one or more subwaveforms within the Q, R, S, and T waveforms or in an interval between the Q, R, S, and T waveforms and displaying at least one conduction timing value for at least one subwaveform of the one or more subwaveforms is provided. Returning to FIG. 8, the ECG system includes two or more electrodes 810, a detector 820, a signal processor 830, and a display device 840.

Two or more electrodes 810 are placed proximate to a beating heart that receive electrical impulses from the beating heart. Two or more electrodes 810 are shown in FIG. 8 as noninvasive electrodes that are attached to the skin of a patient. In various embodiments, two or more electrodes 810 can be invasive electrodes placed directly on the surface of the heart or within heart tissue.

Detector 820 is electrically connected to two or more electrodes 810. Detector 820 detects the electrical impulses from at least one pair of electrodes of the two or more electrodes 810. Detector 820 converts the electrical impulses to an ECG waveform for each heartbeat of the beating heart. Detector 820, for example, samples the electrical impulses. In various embodiments, detector 820 further amplifies the ECG waveform. In various embodiments, detector 820 further performs analog to digital (A/D) conversion on the ECG waveform. In various embodiments, detector 820 provides an ECG waveform with a higher signal-to-noise (S/N) ratio than conventional ECG devices.

Signal processor 830 is electrically connected to detector 820. Signal processor receives the ECG waveform from detector 820. Signal processor 830 detects one or more subwaveforms within Q, R, S, and T waveforms of the ECG waveform or in an interval between the Q, R, S, and T waveforms that represent the depolarization or repolarization of anatomically distinct layers of the ventricles of the beating heart. Signal processor 830 calculates a conduction timing value for each of the one or more subwaveforms for each electrode of the two or more electrodes for each heartbeat of the beating heart.

Signal processor 830 can be a separate device, can be software running on device of detector 820 or display device 840, or can be software running on a remote server and communicating with detector 820 and display device 840 through one or more communication devices. Signal processor 830 can be a separate device that includes, but is not limited to, an application specific integrated circuit (ASIC) or a field programmable gate array (FPGA) or a general purpose processor. A general purpose processor can include, but is not limited to, a microprocessor, a micro controller, or a computer such as the system shown in FIG. 1. Signal processor 830 can be software implemented on another processor of the ECG device, such as a processor of display device 840. Signal processor 830 can also be a remote server that receives the detected and amplified difference voltage signal from detector 820.

Display device 840 displays at least one conduction timing value for at least one subwaveform of the one or more subwaveforms for each electrode of the two or more electrodes for at least one heartbeat of the beating heart. As described above, display device 840 can be an electronic display device including, but not limited to, a cathode ray tube (CRT) device, light emitting diode (LED) device, or Liquid crystal display (LCD) device. Display device 840 can also be a printer device or any combination of an electronic display device and a printer. Additionally, display device 840 can include a memory device to record saah ECG waveforms, saah ECG data and conventional ECG waveforms and data. The memory device can be, but is not limited to, a volatile electronic memory, such as random access memory (RAM), a non-volatile electronic memory, such as electrically erasable programmable read-only memory (EEPROM or Flash memory), or a magnetic hard drive.

In various embodiments, the at least one subwaveform represents depolarization of an anatomically distinct layer of the ventricles. Display device 840 displays the at least one timing value for the at least one subwaveform and a timing value for every other subwaveform of the one or more subwaveforms that represents a depolarization of an anatomically distinct layer of the ventricles.

In various embodiments, the at least one subwaveform represents repolarization of an anatomically distinct layer of the ventricles. Display device 840 displays the at least one timing value for the at least one subwaveform and a timing value for every other subwaveform of the one or more subwaveforms that represents a repolarization of an anatomically distinct layer of the ventricles.

In various embodiments, the two or more electrodes include 12 electrodes. The 12 electrodes are positioned in both the transverse and frontal planes, for example.

In various embodiments, display device 840 further displays the ECG waveform for at least one heartbeat of the beating heart.

In various embodiments, the two or more subwaveforms include 20 subwaveforms representing depolarization and repolarization of 10 layers of the ventricles.

In various embodiments, display device 840 further displays at least one timing value, in a color and/or pattern. Display device 840 then further displays a cross sectional diagram of showing muscle layers of a ventricle of a heart with a layer of the ventricle corresponding to the at least one timing value depicted in the color and/or pattern.

Method for Digitizing Conduction Information

Figure 26:
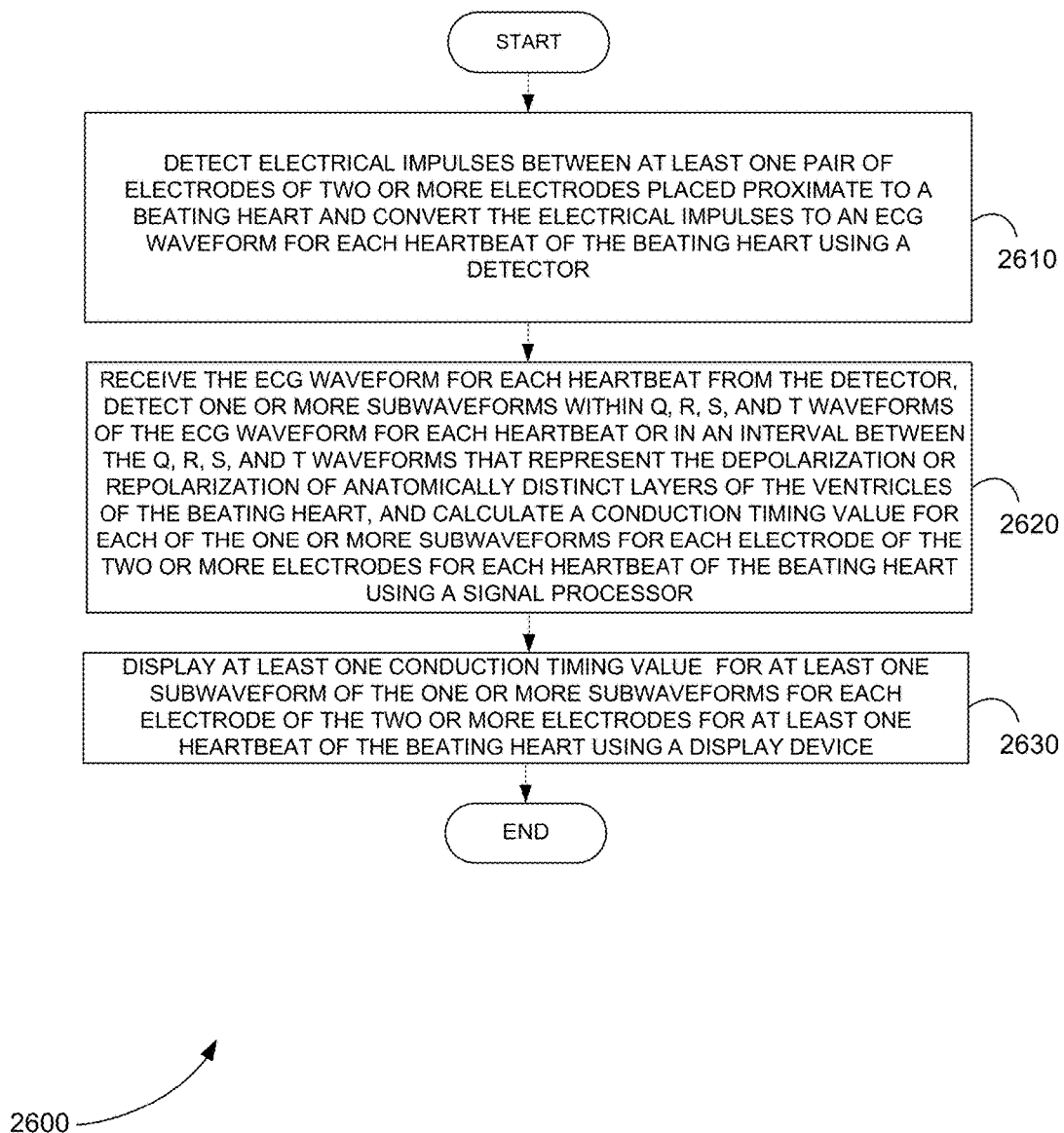
FIG. 26 is a flowchart showing a method for detecting one or more subwaveforms within the Q, R, S, and T waveforms or in an interval between the Q, R, S, and T waveforms and displaying at least one conduction timing value for at least one subwaveform of the one or more subwaveforms, in accordance with various embodiments.

FIG. 26 is a flowchart showing a method 2600 for detecting one or more subwaveforms within the Q, R, S, and T waveforms or in an interval between the Q, R, S, and T waveforms and displaying at least one conduction timing value for at least one subwaveform of the one or more subwaveforms, in accordance with various embodiments.

In step 2610 of method 2600, electrical impulses are detected between at least one pair of electrodes of two or more electrodes placed proximate to a beating heart using a detector. The electrical impulses are converted to an ECG waveform for each heartbeat of the beating heart using the detector.

In step 2620, the ECG waveform for each heartbeat is received from the detector using a signal processor. One or more subwaveforms within Q, R, S, and T waveforms of the ECG waveform for each heartbeat or in an interval between the Q, R, S, and T waveforms are detected that represent the depolarization or repolarization of anatomically distinct layers of the ventricles of the beating heart using a signal processor. A conduction timing value is calculated for each of the one or more subwaveforms for each electrode of the two or more electrodes for each heartbeat of the beating heart using the signal processor.

In step 2630, at least one conduction timing value is displayed for at least one subwaveform of the one or more subwaveforms for each electrode of the two or more electrodes for at least one heartbeat of the beating heart using a display device.

The foregoing disclosure of the preferred embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

What is claimed is:

1. A noninvasive electrocardiography (ECG) system for detecting one or more subwaveforms within the Q, R, S, and T waveforms or in an interval between the Q, R, S, and T waveforms and displaying at least one conduction timing value for at least one subwaveform of the one or more subwaveforms, comprising:
   two or more electrodes adapted to be located near a beating heart of a patient and attached to the skin of the patient that receive electrical impulses from the beating heart;
   a detector that detects the electrical impulses from at least one pair of electrodes of the two or more electrodes and converts the electrical impulses to an ECG waveform for each heartbeat of the beating heart;
   a signal processor that receives the ECG waveform for each heartbeat from the detector, detects one or more subwaveforms within Q, R, S, and T waveforms of the ECG waveform or in an interval between the Q, R, S, and T waveforms that represent the depolarization or repolarization of anatomically distinct layers of the ventricles of the beating heart, and calculates a conduction timing value for each of the one or more subwaveforms for each electrode of the two or more electrodes for each heartbeat of the beating heart; and
   a display device that displays at least one conduction timing value for at least one subwaveform of the one or more subwaveforms for each electrode of the two or more electrodes for at least one heartbeat of the beating heart.

2. The ECG system of claim 1, wherein the at least one subwaveform represents depolarization of an anatomically distinct layer of the ventricles.

3. The ECG system of claim 2, wherein the display device displays the at least one timing value for the at least one subwaveform and a timing value for every other subwaveform of the one or more subwaveforms that represents a depolarization of an anatomically distinct layer of the ventricles.

4. The ECG system of claim 1, wherein the at least one subwaveform represents repolarization of an anatomically distinct layer of the ventricles.

5. The ECG system of claim 4, wherein the display device displays the at least one timing value for the at least one subwaveform and a timing value for every other subwaveform of the one or more subwaveforms that represents a repolarization of an anatomically distinct layer of the ventricles.

6. The ECG system of claim 1, wherein the two or more electrodes comprise 12 electrodes.

7. The ECG system of claim 6, wherein the 12 electrodes are positioned in both the transverse and frontal planes.

8. The ECG system of claim 1, wherein the display device further displays the ECG waveform for at least one heartbeat of the beating heart.

9. The ECG system of claim 1, wherein the two or more subwaveforms comprise 20 subwaveforms representing depolarization and repolarization of 10 layers of the ventricles.

10. The ECG system of claim 1, wherein the display device further displays near the at least one timing value a color and/or pattern.

11. The ECG system of claim 10, wherein the display device further displays a cross sectional diagram of showing muscle layers of a ventricles of a heart with a layer of the ventricles corresponding to the at least one timing value depicted in the color and/or pattern.

12. An invasive electrocardiography (ECG) system for detecting one or more subwaveforms within the Q, R, S, and T waveforms or in an interval between the Q, R, S, and T waveforms and displaying at least one conduction timing value for at least one subwaveform of the one or more subwaveforms, comprising:
   two or more electrodes adapted to be placed directly on the surface of a beating heart of the patient that receive electrical impulses from the beating heart;
   a detector that detects the electrical impulses from at least one pair of electrodes of the two or more electrodes and converts the electrical impulses to an ECG waveform for each heartbeat of the beating heart;
   a signal processor that receives the ECG waveform for each heartbeat from the detector, detects one or more subwaveforms within Q, R, S, and T waveforms of the ECG waveform or in an interval between the Q, R, S, and T waveforms that represent the depolarization or repolarization of anatomically distinct layers of the ventricles of the beating heart, and calculates a conduction timing value for each of the one or more subwaveforms for each electrode of the two or more electrodes for each heartbeat of the beating heart; and
   a display device that displays at least one conduction timing value for at least one subwaveform of the one or more subwaveforms for each electrode of the two or more electrodes for at least one heartbeat of the beating heart.

13. The ECG system of claim 12, wherein the at least one subwaveform represents depolarization of an anatomically distinct layer of the ventricles.

14. The ECG system of claim 13, wherein the display device displays the at least one timing value for the at least one subwaveform and a timing value for every other subwaveform of the one or more subwaveforms that represents a depolarization of an anatomically distinct layer of the ventricles.

15. The ECG system of claim 12, wherein the at least one subwaveform represents repolarization of an anatomically distinct layer of the ventricles.

16. The ECG system of claim 15, wherein the display device displays the at least one timing value for the at least one subwaveform and a timing value for every other subwaveform of the one or more subwaveforms that represents a repolarization of an anatomically distinct layer of the ventricles.

17. The ECG system of claim 12, wherein the two or more electrodes comprise 12 electrodes.

18. The ECG system of claim 17, wherein the 12 electrodes are positioned in both the transverse and frontal planes.

19. The ECG system of claim 12, wherein the display device further displays the ECG waveform for at least one heartbeat of the beating heart.

20. The ECG system of claim 12, wherein the two or more subwaveforms comprise 20 subwaveforms representing depolarization and repolarization of 10 layers of the ventricles.

* * * * *